United States Patent
Hayes et al.

(10) Patent No.: US 11,666,280 B2
(45) Date of Patent: Jun. 6, 2023

(54) CATHETER HAVING A FIBER OPTIC FORCE SENSOR WITH A MIRROR HAVING A PATTERNED REFLECTANCE

(71) Applicant: Lake Region Manufacturing, Inc., Chaska, MN (US)

(72) Inventors: John Michael Hayes, Cork (IE); James F. Kelley, Coon Rapids, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 17/832,975

(22) Filed: Jun. 6, 2022

(65) Prior Publication Data
US 2023/0000437 A1    Jan. 5, 2023

Related U.S. Application Data

(60) Provisional application No. 63/217,985, filed on Jul. 2, 2021.

(51) Int. Cl.
*A61B 5/00* (2006.01)
*A61B 18/00* (2006.01)

(52) U.S. Cl.
CPC .......... *A61B 5/6852* (2013.01); *A61B 5/0066* (2013.01); *A61B 5/0084* (2013.01); *A61B 2018/00577* (2013.01)

(58) Field of Classification Search
CPC ... A61B 5/6852; A61B 5/0066; A61B 5/0084; A61B 2018/00577; A61B 2018/00303; A61B 2018/00345; A61B 18/082; A61B 18/1492

USPC ........................................................... 250/15
See application file for complete search history.

(56) References Cited

U.S. PATENT DOCUMENTS

| | | | |
|---|---|---|---|
| 2011/0087112 A1* | 4/2011 | Leo .................. | A61B 90/98 600/478 |
| 2014/0046194 A1* | 2/2014 | Erdman .......... | A61M 25/0074 606/41 |
| 2017/0100606 A1* | 4/2017 | Lilge .................. | A61N 5/062 |
| 2020/0402228 A1* | 12/2020 | Talbert .............. | A61B 1/0646 |

* cited by examiner

*Primary Examiner* — Jason L McCormack
(74) *Attorney, Agent, or Firm* — Michael F. Scalise

(57) ABSTRACT

An ablation catheter Has a spring assembly residing between an ablation head and a proximal catheter body. Three optical fibers extend through a lumen in the catheter body. Three mirrors supported by the ablation head face proximally but are spaced distally from the optical fibers. The mirrors are provided with a pattern of reflectance that varies along a radius from a central area of reflectance. Light of a respective defined power shines from each of the optical fibers to a corresponding one of the mirrors with a reflected percentage of the respective defined light power being reflected back to the optical fiber. A percentage of the reflected percentage of the respective defined light power is captured by and travels along each optical fiber to a dedicated light wave detector connected to a controller. From the percentage of the reflected percentage of the light of the respective defined power received by each detector, the controller is programmed to calculate whether an axial or lateral force is imparted to the ablation head and, if so, the magnitude and vector of those forces.

28 Claims, 11 Drawing Sheets

CATHETER HAVING A FIBER OPTIC FORCE SENSOR WITH A MIRROR HAVING A PATTERNED REFLECTANCE

CROSS-REFERENCED TO RELATED APPLICATION

This application claims priority to U.S. provisional application Ser. No. 63/217,985, filed on Jul. 2, 2021.

BACKGROUND OF THE INVENTION

1. Field of the Invention

The present invention relates to the field of medical devices, and specifically to catheters for performing various diagnostic and therapeutic medical procedures where the depth of an ablation needs to be controlled. More specifically, the present invention relates to ablation catheters for treating cardiac arrhythmias by ablating near pulmonary venous tissue. Other exemplary uses for the present ablation catheters include the treatment of hypertension and ablation of renal tissue.

An ablation catheter according to the present invention includes an ablation head/spring assembly connected to the distal end of the main catheter body. A proximally-facing mirror having varied light reflectivity across its surface is supported at the proximal end of the ablation head. A system of optical fibers extending to a distal end of the main catheter body is spaced proximally from the mirror. When light from the optical fibers shines on the mirror, its varied light reflectivity is used to indicate to the surgeon the amount of force that the ablation head is exerting on the myocardial tissue during the ablation procedure. Optionally, the varied light reflectivity of the mirror is used to indicate the exact orientation of the catheter body and its ablation head inside the vasculature.

2. Prior Art

The human heart routinely experiences electrical impulses traversing its many surfaces and ventricles, including the left atrium. Just prior to each heart contraction, the heart depolarizes and repolarizes as electrical currents spread across the heart and throughout the body. In healthy hearts, the surfaces and ventricles of the heart experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist because of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. These conditions are associated with a variety of ailments, including death.

Catheters are used in a variety of diagnostic and therapeutic medical procedures to diagnose and correct conditions such as atrial arrhythmia, including for example, ectopic atrial tachycardia, atrial fibrillation, and atrial flutter. Typically, in such a procedure, a catheter carrying one or more electrodes is moved through a patient's vasculature to the heart under fluoroscopy-guided observation. The electrodes may be used for mapping, ablation, diagnosis, or other treatments.

When an ablation therapy is desired to alleviate symptoms including atrial arrhythmia, the ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that can lead to arrhythmias. The ablation catheter may utilize ablative energy including, for example, radio-frequency (RF), cryoablation, laser, chemical, and high-intensity focused ultrasound.

Ablation therapies are often delivered by making many individual ablations in a controlled fashion to form a lesion line. To improve conformity of the individual ablations along the lesion line, it is desirable to precisely control the orientation of the catheter and its ablation head when the individual ablations are conducted, the contact force between the ablation head and the targeted tissue, and the ablation period. Thus, ablation therapies require accurate positioning of the ablation catheter as well as precise pressure exertion for optimal ablative-energy transfer into the targeted myocardial tissue. Inaccurate positioning of the ablation head in the myocardia may result in suboptimum ablation or inadvertent ablation of healthy tissue. Excess force between the ablation head and the targeted myocardial tissue may result in excessive ablation, which may permanently damage cardiac muscle and surrounding nerves. On the other hand, when the contact force between the ablation head and the targeted myocardial tissue is below a target force, the efficacy of the ablation therapy may be reduced.

Thus, for a successful outcome, it is not enough to precisely control the applied force of the ablation head against myocardial tissue under conventional fluoroscopy-guided locational observation. Instead, it is important to precisely control both the force exerted by the ablation head against myocardial tissue and the orientation of the ablation catheter in the myocardium. Both are required.

Therefore, there is a need for an improved ablation catheter that is suitable for performing various diagnostic and therapeutic medical procedures to diagnose and correct conditions, such as atrial arrhythmia, where both the orientation of the catheter in the vasculature and the force exerted by the ablation head against myocardial tissue are precisely controlled. The present ablation catheter provides these advantages.

SUMMARY OF THE INVENTION

To overcome the shortcomings of conventional methods for tracking the path of an ablation catheter through the vasculature to the target myocardial tissue, an ablation catheter according to the present invention has a spring assembly connected between the distal end of a main catheter body and an ablation head. At least three optical fibers are supported by the catheter body. At least three mirrors, each of whose light reflectivity varies across its surface, is supported by the ablation head. The mirrors face proximally but are spaced distally from the distal face of a corresponding one of the optical fibers.

In use, each of the at least three optical fibers is optically connected to a light source and a light power detector. Light of a defined power emitted by the light source into each optical fiber shines on the corresponding mirror and a percentage of the defined light power (a reflected light percentage) is reflected toward the optical fiber. Then, a percentage of the reflected light percentage is captured by and travels down each optical fiber to a dedicated light power detector connected to a controller.

In other words, a percentage of the light power emitted by the light source into each optical fiber is reflected by the corresponding mirror toward the distal face of the optical fiber. Then, a lesser percentage of the reflected light percentage is captured by (a captured light percentage) and travels back down the optical fiber to the light power detector. The detector is configured to determine the intensity or power in the reflected and captured light with respect to the defined power of the light emitted by the light source into the optical fiber. The reflected and captured light received by the light power detector has a somewhat lesser power than the originally emitted light. The controller is programmed to determine the difference between the power of the originally emitted light and that of the reflected and captured light received by the detector and to convert that difference into a force imparted to the ablation head in the vasculature.

For example, in a neutral orientation without any axial or lateral forces imparted to the ablation head, the ablation head is aligned along the longitudinal axis of the catheter body with each of the mirrors spaced a first distance from the distal face of the at least three optical fibers. Then, with only an axial force but no lateral force imparted to the ablation head, the ablation head is still axially aligned with the main catheter body, but now the mirrors are at a second, lesser distance from the distal face of each of the at least three optical fibers. Since the mirrors are closer to the distal faces of the optical fibers, the diminution in power of the reflected and captured light that travels back down each of the optical fibers to the dedicated light power detector is less than with the mirror at the first, greater distance from the optical fibers. In other words, the power of the reflected and captured light is greater with the mirrors at a closer distance to the distal face of each of the at least three optical fibers. The controller connected to the light power detectors is programmed to convert the difference in reflected and captured light power with the mirrors spaced at the first and second distances from the distal faces of the at least three optical fibers into a magnitude of the axial force imparted to the ablation head.

Further, according to the present invention, the mirrors are provided with a patterned reflectance that varies along a radius from a central area of reflectance. The patterned reflectance of the mirrors means that the position of the ablation head in an x, y, z coordinate system can be performed with precise accuracy. The patterned reflectance of the mirrors comprises a central area of reflectance having a first light reflectance $R_1$ and at least one annular ring of reflectance having a second light reflectance $R_2$. Reflectance $R_1$ is different than reflectance $R_2$.

In the case without any axial or lateral force imparted to the ablation head, first percentages of the defined light power from each of the mirror reflectances $R_1$ and $R_2$ are reflected toward the distal face of the corresponding optical fiber. Then, second, lesser percentages of the first percentages are captured by and travel down the optical fiber to the light power detector connected to the controller. The first percentages are less than the defined light power that was initially emitted into the optical fiber by the light source and the second percentages are less than the first percentages.

In the situation with only an axial force imparted to the ablation head, the ablation head is still axially aligned with the main catheter body, but the mirrors are spaced a second distance from the distal face of each of the at least three optical fibers. The second distance is less than the first distance. In this orientation, axial force dependent reflected and captured percentages of the defined light power from the mirror reflectances $R_1$ and $R_2$ are received by the controller via each of the optical fibers. The controller then calculates the magnitude of the axial force imparted to the ablation head by comparing reflected and captured percentages of light power from the mirror reflectances $R_1$ and $R_2$ without any axial force to that of the reflected and captured percentages of the defined light power from the mirror reflectances $R_1$ and $R_2$ under the imparted axial force to determine the distance the ablation head has moved along a longitudinal axis, and hence the magnitude of the axial force imparted to the ablation head.

The magnitude of the axial force is based on Hooke's law, which states that the force (F) needed to extend or compress a spring by some distance (x) scales linearly with respect to that distance. That is, $F_s=kx$, where k is a constant factor characteristic of the spring (i.e., its stiffness), and x is small compared to the total possible deformation of the spring.

Continuing, in the situation where both axial and lateral forces are imparted to the ablation head, the ablation head deflects out of both axial and lateral alignment with respect to the main catheter body and the distal faces of each of the optical fibers. Each mirror is now spaced a third distance from the distal face of each of the at least three optical fibers, the third distance being different than the first and second distances. In comparison to the reflected and captured percentages of the defined light power from the mirror reflectances $R_1$ and $R_2$ without any axial force or with only an axial force, axial and lateral force induced reflected and captured percentages of the defined light power from the mirror reflectances $R_1$ and $R_2$ reflect toward the distal face of each of the optical fibers with a different percentage of the reflected light power captured by and traveling along each of the optical fibers to the corresponding light power detector. The controller calculates the magnitude and vector of the axial and lateral forces imparted to the ablation head from the reflected and captured percentages of the defined light power from the reflectances $R_1$ and $R_2$ of each of the at least three mirrors in comparison to those percentages without any axial force or with only an axial force imparted to the ablation head. It is that each of the at least three mirrors have at least the two mirror reflectances $R_1$ and $R_2$ that enables the controller to determine the magnitude of the axial and lateral forces imparted to the ablation head of the catheter. The axial and lateral force vectors are related to the precise pressure being exerted by the ablation head against the targeted myocardial tissue and, in turn, the ablative-energy being transferred into the myocardial tissue.

In addition to determining the amount of force that the ablation head is exerting against body tissue, for example, myocardial tissue, the controller is programmed to use the axial and lateral forces imparted to the ablation head to determine an exact orientational value in an x, y, z coordinate system of the ablation head out of axial alignment with the main catheter body. The controller is programmed to present the orientational and force data in real-time on a visual display.

If desired, each of the at least three mirrors have a patterned reflectance comprising the central area of reflectance having the first light reflectance $R_1$ and at least a first, second, and third annular rings of reflectance having respective second, third and fourth light reflectances $R_2$, $R_3$ and $R_4$ at progressively greater first, second and third radial distances from the central area of reflectance; the mirror reflectances $R_1$, $R_2$, $R_3$ and $R_4$ are different from each other.

In a further embodiment of an ablation catheter according to the present invention, the patterned reflectances comprising the central area of reflectance $R_1$ and the second, third and fourth reflectances $R_2$, $R_3$ and $R_4$ of the respective first, second and third annular rings of reflectance are each divided into quadrants of reflectances; the quadrants of reflectances of each of the mirror reflectances $R_1$, $R_2$, $R_3$ and $R_4$ are different from each other.

Moreover, in another embodiment of an ablation catheter according to the present invention, the patterned reflectance comprising the central area of reflectance $R_1$ and the second, third and fourth reflectances $R_2$, $R_3$ and $R_4$ of the respective first, second and third annular rings of reflectance are each divided into fractional segments of reflectances; the fractional segments of reflectances of each of the mirror reflectances $R_1$, $R_2$, $R_3$ and $R_4$ are different from each other.

If desired, the controller also uses the force data at the ablation head to generate an input signal to an electromechanical vibrator integrated into the catheter's handle so that the surgeon receives force feedback at the hand. This increased feedback to the surgeon helps reduce the risk of damaging vasculature tissue, speeds up medical procedures and reduces contrast fluid and x-ray use. Also, the force data correlates with the contact force between the ablation head and the targeted tissue. Ablation therapies require accurate positioning of the ablation catheter as well as precise pressure exertion for optimal ablative-energy transfer into the targeted myocardial tissue. Excess force between the ablation head and the targeted myocardial tissue may result in excessive ablation, which may permanently damage cardiac muscle and surrounding nerves. Conversely, when the contact force between the ablation head and the myocardial tissue is below a target force, the efficacy of the ablation therapy may be reduced.

Further embodiments of an ablation catheter according to the present invention include push-pull wires extending from the handle connected to a proximal end of the catheter to the ablation head. Manipulation of actuators in the handle move the push-pull wires to selectively deflect the ablation head. As previously discussed, in addition to being programmed to determine the amount of force that the ablation head is exerting against myocardial tissue, the controller is programmed to use the reflected and captured light power percentages of the defined light power from the at least two reflectances $R_1$ and $R_2$ of each of the at least three mirrors in comparison to those percentages without any axial force or with only an axial force imparted to the ablation head to determine an exact orientational value of the ablation head out of axial alignment with the catheter sidewall. In this embodiment, the orientation of the ablation head caused by manipulation of the push-pull wires is first ascertained and then when the ablation head is pressed against myocardial tissue, any added change in the reflected and captured light power percentages of the defined light power from the at least two reflectances $R_1$ and $R_2$ of each of the at least three mirrors in comparison to those percentages without any axial force or with only an axial force imparted to the ablation head is used to calculate the additional force vector resulting from contact with myocardial tissue.

These and other aspects of the present invention will become increasingly more apparent to those skilled in the art by reference to the following detailed description and to the appended drawings.

DETAILED DESCRIPTION OF THE PREFERRED EMBODIMENTS

Figure 1:
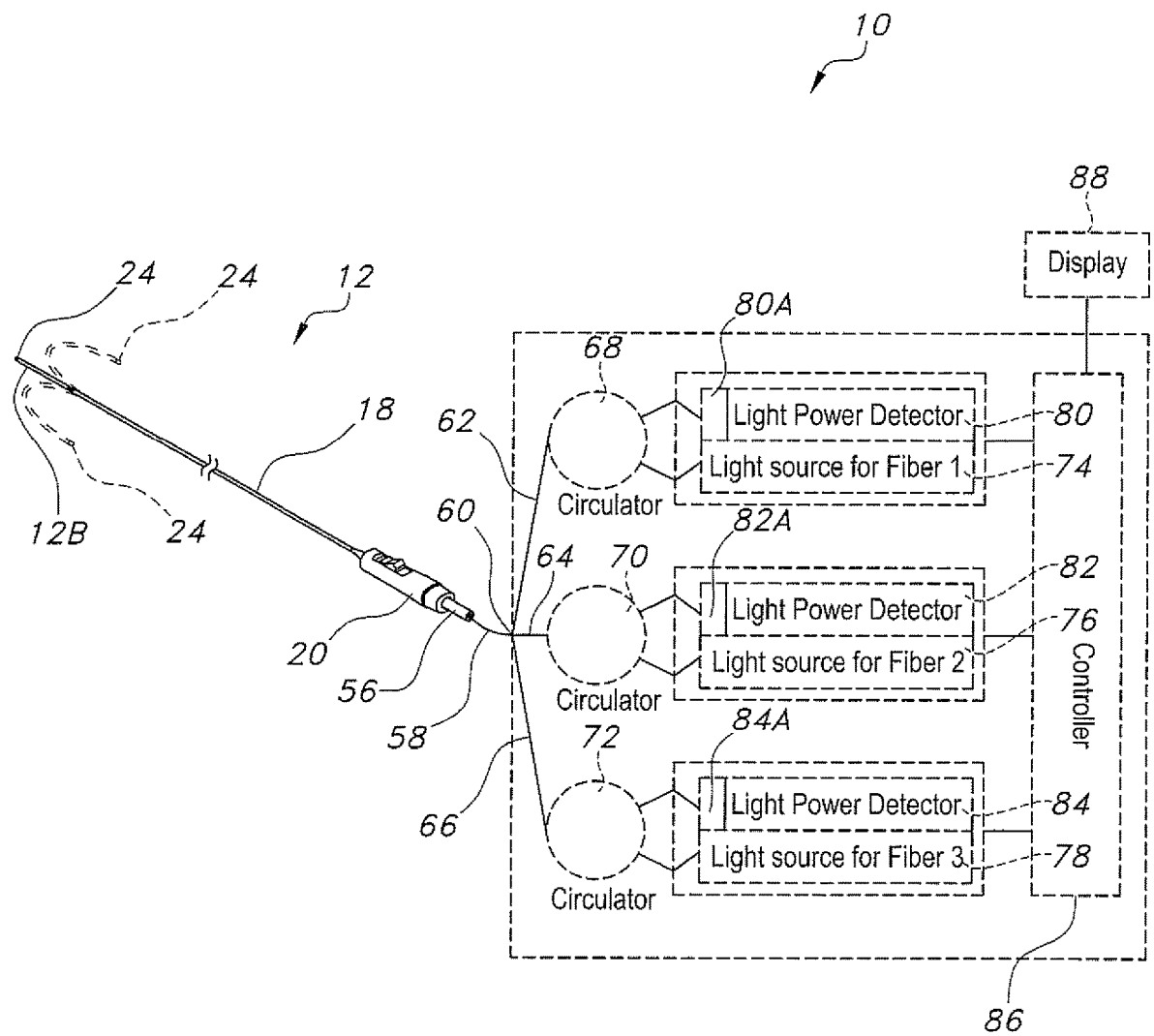
FIG. 1 is a schematic view of an exemplary ablation catheter system 10 comprising an ablation catheter 12 having at least three mirrors corresponding to respective optical fibers extending to a handle 20 connected to an optical connector 56 and an external optical cable 58 supporting external optical fibers 62, 64 and 66 optically connected to respective light sources 74, 76 and 78 and light power detectors 80, 82 and 84, all connected to a controller having a visual display 88 according to the present invention.

Turning now to the drawings, FIG. 1 is a schematic of an ablation catheter system 10 according to the present invention. The ablation catheter system 10 comprises an ablation catheter 12 supporting three optical fibers. For the sake of simplicity, only two optical fiber 14 and 16 are shown in FIGS. 2 and 5 to 8. The optical fibers extend to a handle 20 for the ablation catheter 12 where they connect to an optical connector 56 and an external optical cable 58 supporting external optical fibers 62, 64 and 66 optically connected to respective light sources 74, 76 and 78 and light power detectors 80, 82 and 84, all connected to a controller having a visual display 88.

The ablation catheter 12 includes a catheter body 18 which, as an elongate tubular structure, is flexible yet substantially non-compressible along its length. The catheter body 18 connects between the handle 20 and a spring assembly 22 which, in turn, is connected to a distal ablation head 24. As will be described hereinafter, in an exemplary embodiment the handle 20 houses a steering and locking mechanism that provides for selective deflection or steering of the catheter body 18/spring assembly 22/ablation head 24 into any number of disparate orientations within the vasculature of a patient and then for locking the ablation catheter 12 in a desired orientation for performing a medical procedure. FIG. 1 shows the ablation catheter 12 in two generally opposed articulated orientations (depicted in dashed lines) and an unarticulated neutral orientation. In another embodiment, the ablation catheter 12 does not have structure for selective deflection or steering of the catheter body 18/spring assembly 22/ablation head 24. The ablation catheter 12 has a length ranging from about 50 cm to about 350 cm.

Figures 2, 2A:
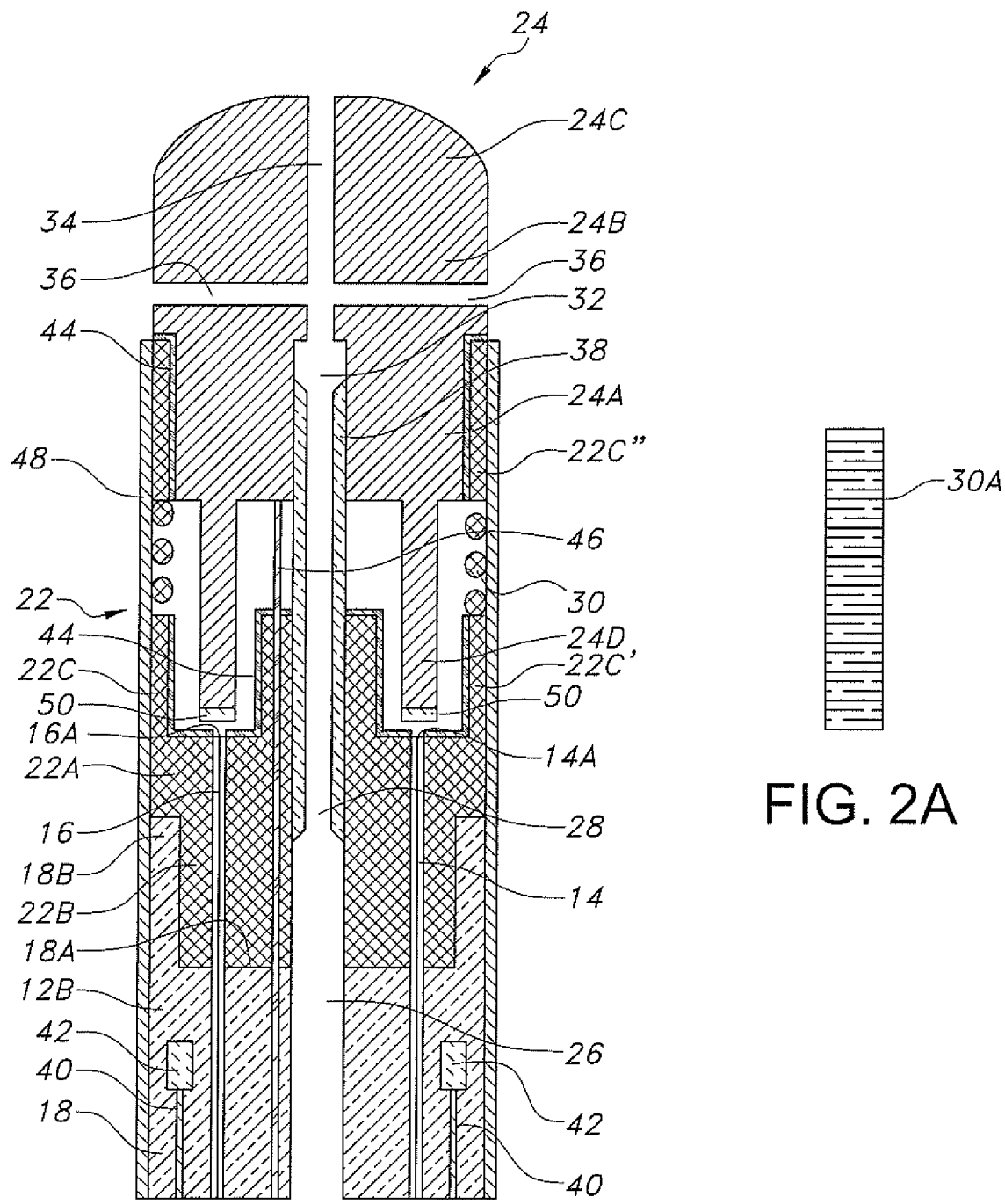
FIG. 2 is a partial cross-sectional view of an ablation catheter 12 shown in FIG. 1.
FIG. 2A illustrates a slotted spring 30A that is useful with the ablation catheter 12 shown in FIGS. 1 and 2.

An exemplary catheter body 18 is a tubular member having a main delivery lumen 26 (FIG. 2) that extends from a catheter proximal portion 12A (FIG. 1) received in the handle 20 to a distal portion 12B connected to the spring assembly 22 in turn connected to the ablation head 24. The catheter body 18 is formed of a polymeric material, such as of PEBAX, encasing a tubular wire braided as a mesh. A liner of a second polymeric material, for example PTFE, resides inside the PEBAX tube. The PTFE liner provides the main delivery lumen 26 with sufficient lubricity so that medical instruments, devices, and the like, slide through the lumen with a minimal amount of force. The main delivery lumen 26 is sized and shaped to receive, for example, instruments, fluids, media, and the like. FIG. 2 illustrates that the main delivery lumen 26 extends to a step 18A of the catheter body 18 that forms a distally-extending outer sleeve portion 18B.

The spring assembly 22 is comprised of a cylindrically-shaped intermediate portion 22A that resides between a proximal connector spring assembly portion 22B of a reduced diameter and a distal sleeve 22C. The proximal connector portion 22B has a diameter that is sized to fit into the step 18A of the catheter body 18. When seated against the step 18A, the intermediate connector portion 22A and the proximal connector portion 22B provide a lumen 28 through the spring assembly 22 that is in open communication with the main delivery lumen 26 through the catheter body 18. The distal sleeve of the spring assembly 22 has a diameter that is the same as that of the intermediate portion 22A and is defined by two sections—a first distal sleeve section 22C' and a second distal sleeve section 22C".

A coil spring 30 of the spring assembly 22 has its proximal end connected to the first distal sleeve section 22C' and its distal end is connected to the second distal sleeve section 22C". The coil spring 30 provides 360° of bending movement of the ablation head 24 secured to the second distal sleeve section 22C" with respect to the first distal sleeve section 22C'.

Alternately, FIG. 2A shows that the spring as a slotted spring 30A residing between the first distal sleeve section 22C' and the second distal sleeve section 22C" of the spring assembly 22. Whether it is a coil spring 30 or a slotted spring 30A, the spring is preferably made of stainless steel or nitinol.

FIG. 2 further illustrates that the ablation head 24 has a cylindrically-shaped proximal head portion 24A extending axially to a stepped intermediate portion 24B connected to a distal atraumatic tip 24C. The atraumatic tip 24C has a dome-shape that is polished smooth to help minimize tissue damage and trauma as the ablation catheter 12 is moved through a vasculature. The cylindrically-shaped proximal head portion 24A has a reduced diameter with respect to the intermediate portion 24B. That way, the second distal sleeve section 22C" is sized and shaped to receive or house the proximal head portion 24A to connect the spring assembly 22 to the ablation head 24. Suitable materials for the ablation head 24 including its atraumatic tip 24C are stainless steel, nickel, titanium, platinum, and platinum/iridium.

A distal lumen 32 extends axially along the proximal head portion 24A, through the intermediate head portion 24B and into the atraumatic tip 24C. The distal lumen 32 is in open communication with the main delivery lumen 26 in the catheter body 12 and the spring assembly lumen 28.

Part-way through the ablation head 24, the distal lumen 32 steps down to a secondary distal lumen 34 that leads to the apex of the atraumatic tip 24C. A plurality of lateral lumens 36 extend radially outwardly from the secondary distal lumen 34 to an outer surface of the intermediate cylindrical portion 24B of the ablation head 24. While two lateral lumens 36 are shown in FIG. 2, it is within the scope of the present invention that a plurality of lateral lumens can communicate laterally from the secondary distal lumen 34 to the outer surface of the intermediate portion 24B and to the distal atraumatic head 24C of the ablation head 24. Preferably the lateral lumens 36 are evenly spaced about the circumference of the ablation head 24. For example, in an embodiment with four lateral lumens 36, the lumens are evenly spaced at 90° intervals from each other. In an embodiment with three lumens 36, the lateral lumens are evenly spaced at 120° interval from each other. However, it is within the scope of the present ablation catheter 12, that the lateral lumens 36 need not be evenly spaced from each other. A flexible inner tube 38 of a polymeric material resides in the spring assembly lumen 28 and the distal lumen 32, seated against the step delineating the proximal ablation head portion 24A from the intermediate portion 24B.

FIG. 2 further shows that in the selectively manipulatable embodiment, the deflectable ablation catheter 12 of the present invention has two push-pull wires 40 anchored to the distal portion 12B of the catheter body 18. The push-pull wires 40 extend proximally from the distal portion 12B to the handle assembly 20. The handle assembly 20 enables a user to selectively manipulate the push-pull wires 40 in a forward or distal direction or in a backwards or proximal direction. That is for selectively deflecting the ablation head 24 in a myriad of orientations out of axial alignment as shown with the dashed lines in FIG. 1. While only two push-pull wires 40 are depicted in FIG. 2, it is understood that is by way of example only. A typical push-pull wire system has four push-pull wires evenly spaced at 90° intervals about the distal portion 12B of the catheter body 18. Moreover, an anchor 42 couples a distal end of each push-pull wire 40 to the distal portion 12B of the catheter body 18.

For a more thorough understanding of handle assemblies that are useful with the present ablation catheter 12, reference is made to U.S. Design Pat. Nos. D612,044 to Scheibe, D638,934 to Kimmel, D653,335 to Kampa et al. and D653,337 to Kampa et al., all of which are assigned to the assignee of the present invention and incorporated herein by reference.

For a more thorough understanding of push-pull wire systems including their anchoring mechanisms that are useful with the present invention, reference is made to U.S.

Pat. Nos. 7,553,305, 8,056,207 and 8,540,697, all to Honebrink et al. and all of which are assigned to the assignee of the present invention and incorporated herein by reference. And, for a more thorough understanding of an anchor for a push-pull wire system, reference is made to U.S. Pat. No. 7,497,853 to Fischer et al., which is assigned to the assignee of the present invention and incorporated herein by reference.

For a more thorough understanding of deflectable catheter steering and locking systems that are useful with the present ablation catheter 12, reference is made to U.S. Pat. No. 7,497,853 to Fischer et al., U.S. Pat. No. 7,588,555 to Pudelko et al., U.S. Pat. No. 7,615,044 to Scheibe et al., U.S. Pat. No. 7,955,314 to Fischer et al., U.S. Pat. No. 8,007,463 to Pudelko et al., U.S. Pat. No. 8,048,026 to Fischer et al., U.S. Pat. No. 8,308,659 to Scheibe et al., U.S. Pat. No. 8,444,626 to Fischer et al., U.S. Pat. No. 8,790,362 to Kimmel et al. and U.S. Pat. No. 9,149,607 to Scheibe et al., all of which are assigned to the assignee of the present invention and incorporated herein by reference.

FIG. 2 also depicts that the spring assembly 22 is electrically isolated from the ablation head 24 by an electrical insulation material 44 and that a power cable 46 is electrically connected to the ablation head 24. The power cable 46 extends proximally from the ablation head 24 to the handle assembly 20. There, it is configured for electrical connection to a power source (not shown) for energizing the ablation head 24 during a medical procedure. With the ablation head 24 electrically energized, the electrical insulation material 44 prevents the spring assembly 22 and catheter body 18 from also being electrically energized.

To ablate tissue, the ablation head 24 is configured to electrically conduct a DC energy current or a radio-frequency energy into the targeted tissue. The ablation catheter 12 of the present invention can also be configured for cryoablation, laser ablation, chemical ablation, and ultrasonic ablation of a target tissue. In other embodiments, the power cable 44 is used to provide electrical power to mapping electrodes (not shown), and the like, supported by the ablation head 24.

Preferably, a lubricious coating 48 is provided on the catheter body 18 and the spring assembly 22, but not the ablation head 24. The lubricious coating 48 helps to reduce friction between the ablation catheter 12 and body tissue as the catheter is moved through a vasculature. Suitable coatings for this purpose are described in U.S. Pat. No. 9,255,173 to Edwards, U.S. Pat. No. 9,623,157 to Edwards, U.S. Pat. No. 9,714,361 to Edwards, and U.S. Pat. No. 10,899,944 to Edwards, and in U.S. Pub. Nos. 2014/0275340 to Edwards and 2016/0160078 to Edwards, all of which are assigned to the assignee of the present invention and incorporated herein by reference. Suitable lubricious coatings are also described in U.S. Pat. No. 7,776,956 to Webster at al. and U.S. Pat. No. 9,676,895 to Harkal et al.

An annular inner sleeve 24D extends proximally from the cylindrically-shaped proximal head portion 24A of the ablation head 24 into the spring assembly 22, spaced radially inwardly with respect to the spring 30 and the first distal sleeve section 22C'. A proximal face of the annular inner sleeve 24D supports three proximally facing highly polished mirrors 50A, 50B and 50C (FIGS. 2, 3, 3A, 4A and 5 to 8). The mirrors 50A, 50B and 50C are axially aligned with the distal face of a respective one of three internal optical fibers 14, 16 and a third optical fiber (not shown). For the sake of clarity, only two optical fibers 14 and 16 are shown in FIGS. 2 and 5 to 8. The internal optical fibers extend from a distal face of the intermediate portion of the spring assembly 22 to the handle assembly 20. With the ablation catheter 12 in a neutral position without any axial or lateral forces imparted to the ablation head 24, each of the highly polished proximally-facing mirrors 50A, 50B and 50C is aligned substantially parallel to the distal end of a respective one of three optical fibers 14, 16 and the third optical fiber (not shown).

The ablation catheter 12 and its optical fibers 14, 16 and the third optical fiber (not shown) are detachably connected to an optical connector 56 (FIG. 1) that is plugged into a receptacle in the handle assembly 20. An external optical cable 58 is connected to the optical connector 56 opposite the ablation catheter 12.

The optical fibers 14, 16 and the third optical fiber (not shown) supported by the ablation catheter 12 are optically connected through the optical connector 56 and the external optical cable 58 to a manifold 60 (FIG. 1) where corresponding external optical fibers 62, 64 and 66 fan out for connection to respective circulators 68, 70 and 72 (circulator 72 is optically connected to the third optical fiber that is not shown in the drawings). The circulators 68, 70 and 72 in turn are optically connected to respective light sources 74, 76 and 78, and light power detectors 80, 82 and 84, all connected to a controller 86 serving as a computer. The controller 86 is connected to a visual display 88.

The first light source 74 emits light of a first power through the first circulator 68 into the external optical fiber 62 optically connected to the optical fiber 14 in the ablation catheter 12. Similarly, the second light source 76 emits light of a second power through the second circulator 70 into the external optical fiber 64 optically connected to the optical fiber 16. Further, the third light source 78 emits light of a third power through the third circulator 72 into the external optical fiber 66 optically connected to the third optical fiber not shown in FIGS. 2 and 5 to 8).

In various embodiments, the light sources 74, 76 and 78 are single wavelength light sources, narrow-band wavelength light sources or broadband wavelength light sources. However, to prevent light from one optical fiber from being reflected into a different optical fiber and for this power then being measured and input into the controller 86, each optical fiber is irradiated with light of a different wavelength (or band of wavelengths) that does not overlap with the light wavelengths irradiating any of the other optical fibers. The light power detector for each optical fiber is only sensitive to the specific light wavelength of its corresponding light source.

Moreover, as shown in FIG. 1, in an exemplary embodiment of the ablation catheter 12, each light power detector 80, 82 and 84 is provided with a filter 80A, 82A and 84A that allows only the correct wavelength or band of wavelengths through to the controller 86. The important aspect of this embodiment is that each of the filters 80A, 82A and 84A does not allow any light through that will overlap with the detected light wavelengths of the other filters. Each light source 74, 76 and 78 irradiates its corresponding optical fiber pairs 14/62, 16/64 and the third internal optical fiber/66 with light of a different wavelength or wavelengths matching the filter 80A, 82A and 84A of the associated power detector 80, 82 and 84. Then, so long as the respective light power detector 80, 82 and 84 is sensitive to the incoming light power, and the detector is configured to output a current or voltage that correlates with the power collected through the respective optical fiber pairs 14/62, 16/64 and the third internal optical fiber/66, the controller 86 is programmed to use the output current or voltage to calculate the magnitude and vector of force imparted to the ablation head 24 and hence the spatial orientation of the ablation catheter 12 in the vasculature. A narrow linewidth laser is suitable for the dedicated light sources 74, 76 and 78. A Superluminescent Light Emitting Diode (SLED) or a scanning laser is a suitable broadband light source.

In another embodiment, there is only one broadband light source that selectively emits light into each optical fiber pair 14/62, 16/64 and the third internal optical fiber/66.

Regardless whether the light sources 74, 76 and 78 are dedicated light sources or the broadband light sources, light reflected by the mirrors 50A, 50B and 50C onto the distal faces of the corresponding optical fibers 14, 16 and the third internal optical fiber (not shown) returns via the optical fibers to the optical connector 56 and the respective external optical fiber 62, 64 and 68 and then the respective circulator 68, 70 and 72.

The circulators 68, 70 and 72 are optically connected to corresponding light power detectors 80, 82 and 84. Each detector analyzes the light it receives to identify the intensity of the light at various powers. As will be described in greater detail hereinafter, this information is forwarded to the controller 86 where the difference in the intensity of the reflected light and then the percentage of the reflected light that is captured by the optical fiber 14, 16 and the third internal optical fiber (not shown) with respect to the intensity of the light originally emitted by the light source into each optical fiber 14, 16 and the third internal optical fiber (not shown) is used to calculate the magnitude of the axial and lateral forces imparted to the ablation head 24 of the catheter 12. The magnitude of the axial and lateral forces imparted to the ablation head 24 in turn is used to calculate the position of the ablation catheter 12 including the ablation head 24 in the vasculature.

Figure 3:
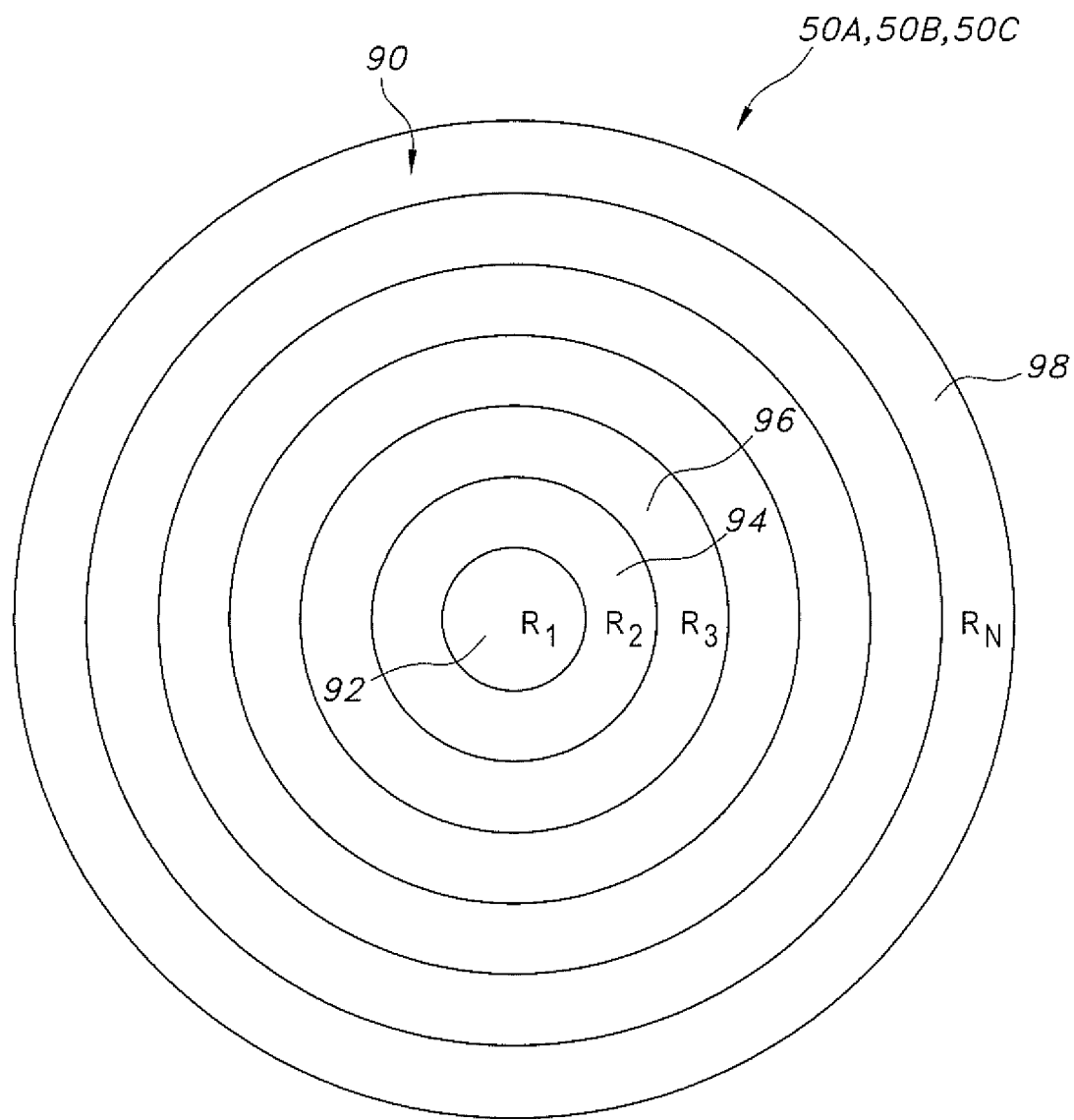
FIG. 3 is a plan view of the reflective surface 90 of the catheter mirrors 50A, 50B and 50C patterned so that light reflectance varies along a radius radiating outwardly from a central area of light reflectivity 92.
Figure 3A:
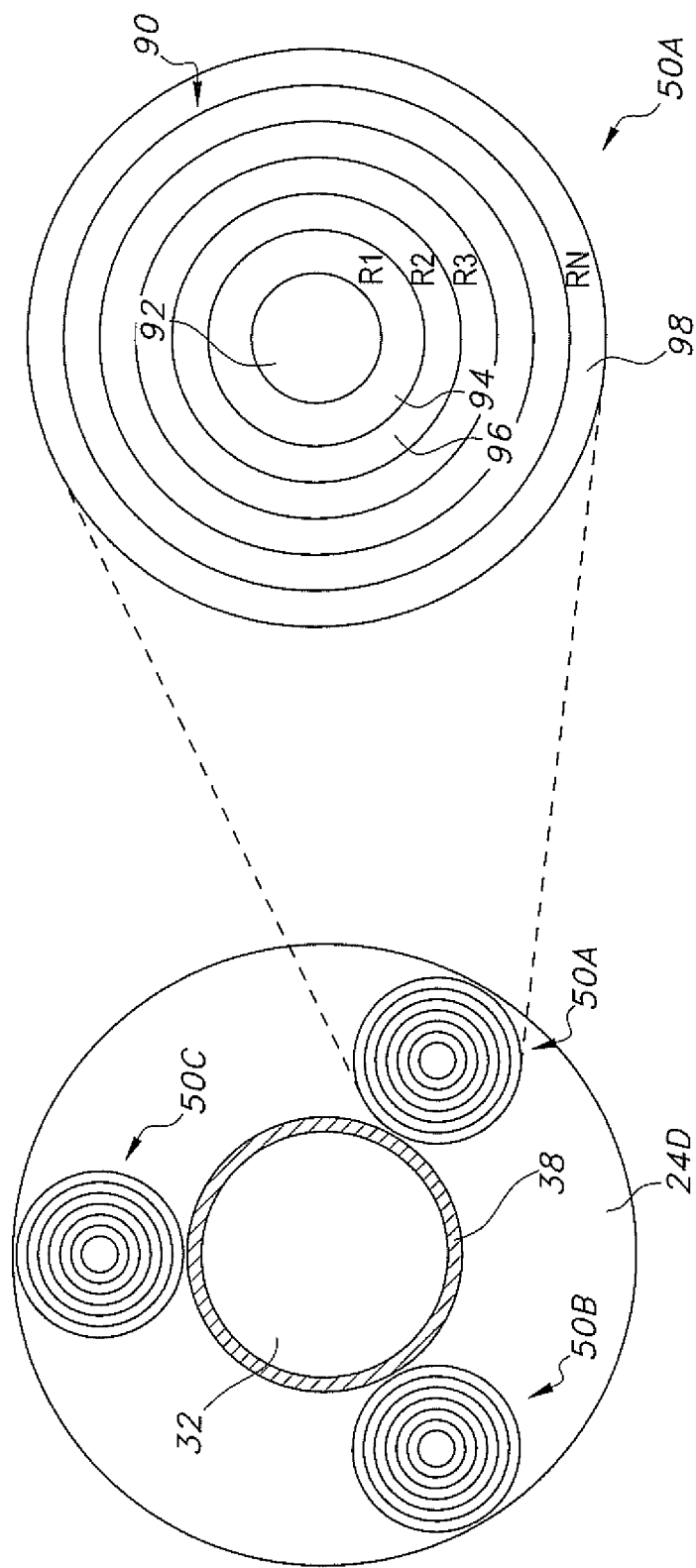
FIG. 3A is a schematic view of the ablation catheter 12 having the mirrors 50A, 50B and 50C shown in FIG. 3 spaced about the circumference of a proximally-extending annular inner sleeve 24D of the ablation head 24 of the catheter shown in FIGS. 1 and 2.

FIGS. 3 and 3A illustrate an embodiment of the ablation catheter 12 that increases the accuracy of the positional measurement of the ablation head 24 in the vasculature. In this embodiment, each of the three mirrors 50A, 50B and 50C is provided with a reflective surface 90 that is patterned so that light reflectivity or light reflectance (the light reflective quality or power of the reflective surface 90) varies along a radius radiating outwardly from a central area of light reflectivity 92. The reflectance of each of the mirrors 50A, 50B and 50C is its effectiveness in reflecting radiant energy. It is the fraction of incident electromagnetic power that is reflected at the mirror 50A, 50B and 50C. Reflectance is a component of the response of the electronic structure of the mirror 50A, 50B and 50C to the electromagnetic field of light, and is in general a function of the frequency, or wavelength, of the light, its polarization, and the angle of incidence. The dependence of reflectance on the wavelength is called a reflectance spectrum or spectral reflectance curve.

In that manner, the first or central area of light reflectivity 92 has a first light reflectivity $R_1$. A first annular band or ring 94 at a first radial distance from the central area of light reflectivity 92 has a second light reflectivity $R_2$, which is different than the first light reflectivity $R_1$. A second annular ring 96 at a second radial distance from the central area of light reflectivity 92 has a third light reflectivity $R_3$, which is different than the first light reflectivity $R_1$ of the central area 92 and the second light reflectivity $R_2$ of the first annular ring 94. This pattern continues radially across the reflective surface 90 of each of the mirrors 50A, 50B and 50C to an outermost annular ring 98 having an nth light reflectivity $R_n$ that is different than the first, second and third light reflectivities $R_1$, $R_2$ and $R_3$ of the respective central area 92, first annular ring 94 and second annular ring 96.

The pattern of varying reflectance of the reflective surface 90 of each of the mirrors 50A, 50B and 50C can be fabricated in the following ways:

a) patterned surface roughening by a laser robotically directed onto the regions to be roughened and controlled by software;

b) surface roughening by applying photoresist, patterning the photoresist using a mask, removing photoresist in the required areas and etching those areas to roughen the reflective surface 90; and c) depositing either reflection or anti-reflection coatings onto the mirror 50A, 50B and 50C and then selectively removing the coating in the required area using masking techniques.

It is noted that the reflective surface 90 of the mirrors 50A, 50B and 50C shown in FIGS. 3 and 3A has six annular rings radiating outwardly from the central area of reflectivity 92. However, that is meant for illustration and should not be taken as limiting the present invention. According to the present invention, there can be more than or less than six annular rings radiating outwardly from a center area of reflectivity. Moreover, the central area of reflectivity need not be circular. If desired, it can have a different shape, for example, a square shape or be a multi-sided closed plane bounded by straight lines (polygon).

Figure 4:
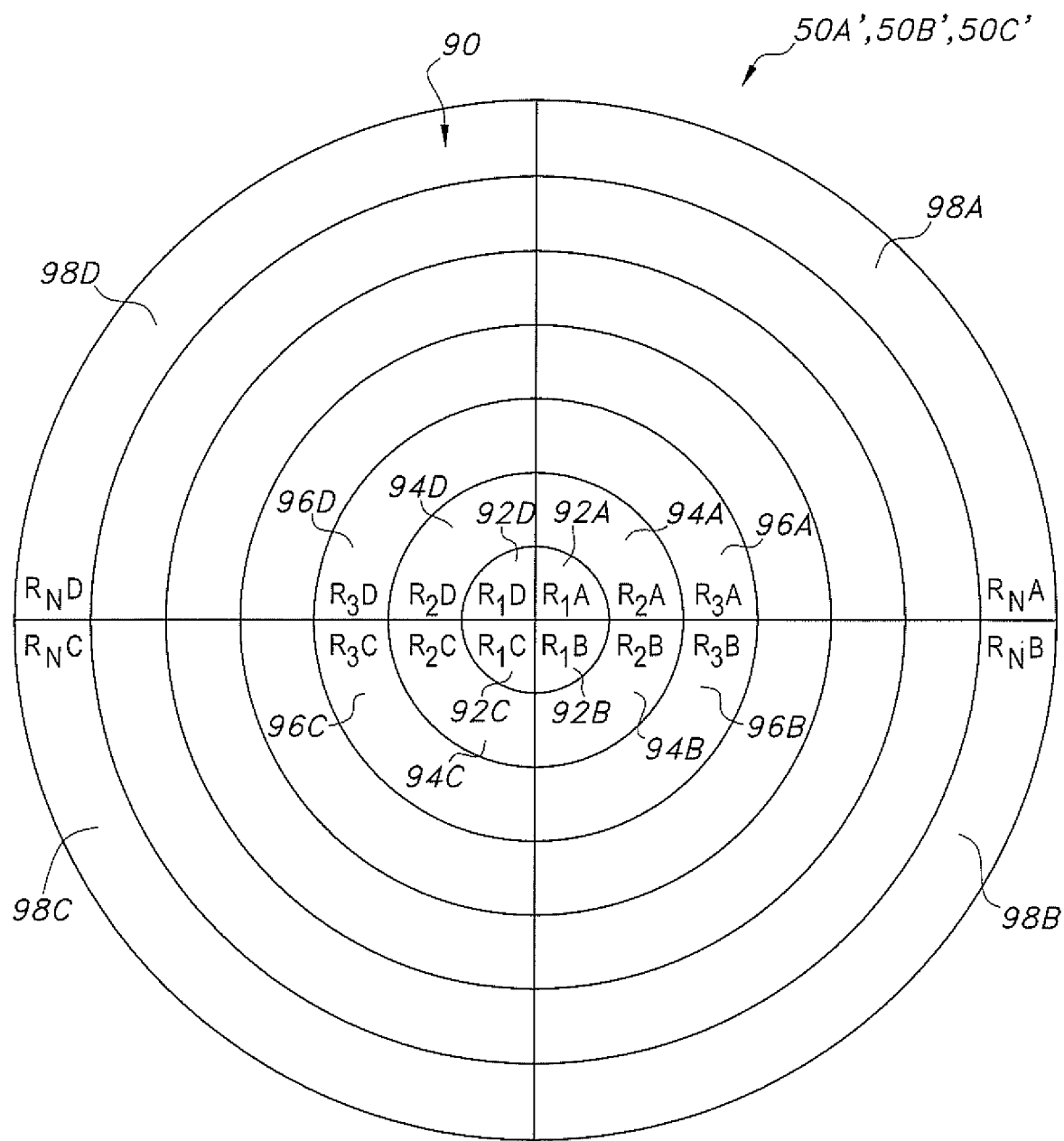
FIG. 4 is a plan view of the reflective surface 90 of the catheter mirrors 50A', 50B' and 50C' similar to those shown in FIG. 3, but with the patterned light reflectances divided into quadrants.
Figure 4A:
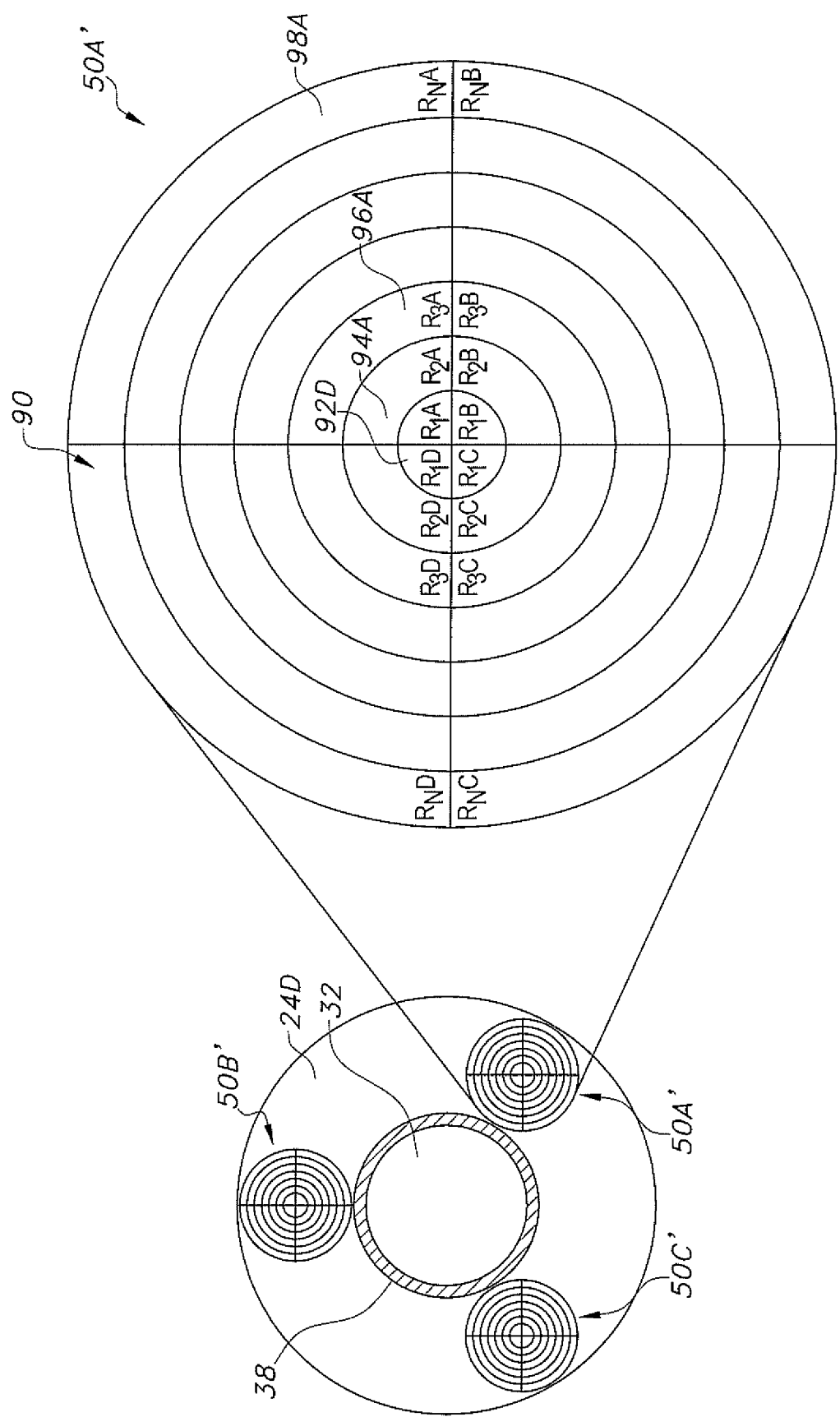
FIG. 4A is a schematic view of the ablation catheter 12 having the mirrors 50A', 50B' and 50C' shown in FIG. 4 spaced about the circumference of a proximally-extending annular inner sleeve 24D of the ablation head 24 of the catheter shown in FIGS. 1 and 2.

FIGS. 4 and 4A illustrate an embodiment of the mirrors 50A', 50B' and 50C' for the ablation catheter 12 of the present invention that further increases the accuracy of the positional measurement of the ablation head 24. In this embodiment, the reflective surface 90 of each of the mirrors 50A', 50B' and 50C' comprises the center or first area of light reflectivity 92 having the first light reflectivity $R_1$, the outwardly radiating annular bands or rings 94, 96 having the respective second and third light reflectivities $R_2$ and $R_3$ and continuing to the outermost annular ring 98 of the nth light reflectivity $R_n$. However, in this embodiment, the center or first area of light reflectivity 92, the first and second annular rings 94, 96 continuing to the nth annular ring 98 are each divided into quadrants.

Specifically, the first light reflectivity $R_1$ of the central area of light reflectivity 92 is divided into a first quadrant 92A of the first light reflectivity $R_1A$, a second quadrant 92B of the first light reflectivity $R_1B$, a third quadrant 92C of the first light reflectivity $R_1C$, and a fourth quadrant 92D of the first light reflectivity $R_1D$. Each of the light reflectivities $R_1A$, $R_1B$, $R_1C$ and $R_1D$ of the respective quadrants 92A, 92B, 92C and 92D is different than the other light reflectivities. The respective light reflectivities are input into the programmable memory of the controller 86.

Similarly, the second light reflectivity $R_2$ of the first ring of light reflectivity 94 is divided into a first quadrant 94A of the second light reflectivity $R_2A$, a second quadrant 94B of the second light reflectivity $R_2B$, a third quadrant 94C of the second light reflectivity $R_2C$, and a fourth quadrant 94D of the second light reflectivity $R_2D$. Each of the light reflectivities $R_2A$, $R_2B$, $R_2C$ and $R_2D$ of the respective quadrants 94A, 94B, 94C and 94D is different with respect to each other and with respect to the light reflectivities $R_1A$, $R_1B$, $R_1C$ and $R_1D$ of the respective quadrants 92A, 92B, 92C and 92D of the central area of light reflectivity 92. The respective light reflectivities are input into the programmable memory of the controller 86.

Further, the third light reflectivity $R_3$ of the second ring of light reflectivity 96 is divided into a first quadrant 96A of the third light reflectivity $R_3A$, a second quadrant 96B of the third light reflectivity $R_3B$, a third quadrant 96C of the third light reflectivity $R_3C$, and a fourth quadrant 96D of the third light reflectivity $R_3D$. Each of the light reflectivities $R_3A$, $R_3B$, $R_3C$ and $R_3D$ of the respective quadrants 96A, 96B, 96C and 96D is different with respect to each other and with respect to the light reflectivities $R_2A$, $R_2B$, $R_2C$ and $R_2D$ of the respective quadrants 94A, 94B, 94C and 94D of the first ring of light reflectivity 94 and with respect to the light reflectivities $R_1A$, $R_1B$, $R_1C$ and $R_1D$ of the respective quadrants 92A, 92B, 92C and 92D of the central area of light reflectivity 92. The respective light reflectivities are input into the programmable memory of the controller 86.

This pattern continues across the reflective surface 90 of each of the mirrors 50A', 50B' and 50C' to the nth light reflectivity $R_n$ of the outermost ring of light reflectivity 98. The nth light reflectivity $R_n$ of the outermost ring of light reflectivity 98 is divided into a first quadrant 98A of the nth light reflectivity $R_nA$, a second quadrant 98B of the nth light reflectivity $R_nB$, a third quadrant 98C of the nth light reflectivity $R_nC$, and a fourth quadrant 98D of the nth light reflectivity $R_nD$. Each of the light reflectivities $R_nA$, $R_nB$, $R_nC$ and $R_nD$ of the respective quadrants 98A, 98B, 98C and 98D is different with respect to each other and with respect to the light reflectivities $R_3A$, $R_3B$, $R_3C$ and $R_3D$ of the respective quadrants 96A, 96B, 96C and 96D of the second ring of light reflectivity 96, with respect to the light reflectivities $R_2A$, $R_2B$, $R_2C$ and $R_2D$ of the respective quadrants 94A, 94B, 94C and 94D of the first ring of light reflectivity 94 and with respect to the light reflectivities $R_1A$, $R_1B$, $R_1C$ and $R_1D$ of the respective quadrants 92A, 92B, 92C and 92D of the central area of light reflectivity 92. This pattern continues across the reflective surface 90 of each of the mirrors 50A', 50B' and 50C' for as many rings of light reflectivity as each mirror has. The respective light reflectivities are input into the programmable memory of the controller 86.

Figure 5:
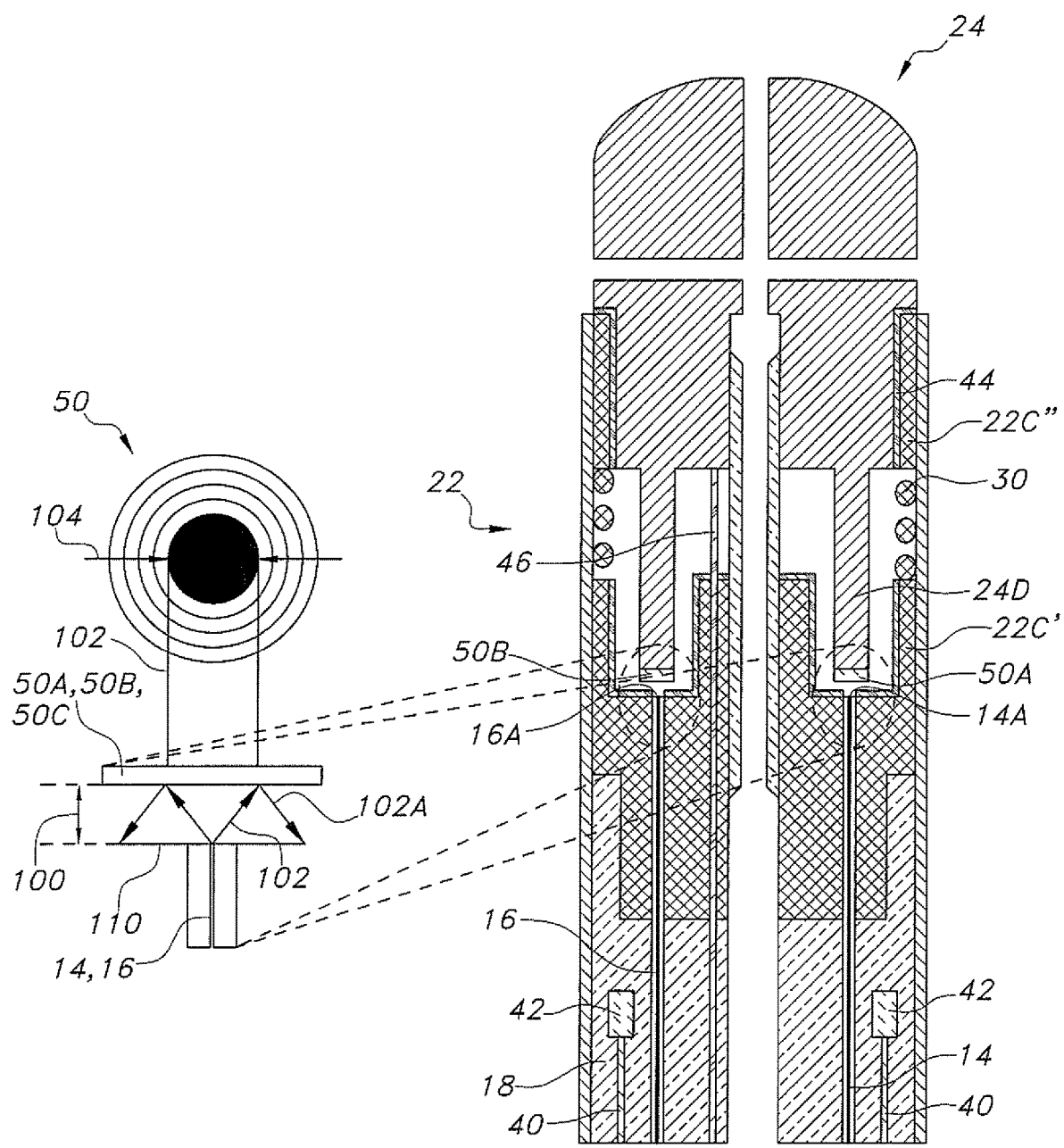
FIG. 5 is a cross-sectional view showing the relative position of two of the mirrors 50A, 50B with respect to the distal faces 14A, 16A of optical fiber 14, 16 without an axial force imparted to the ablation head 24.

FIG. 5 illustrates the ablation catheter 12 in a first or neutral state without any axial or lateral force imparted to the ablation head 24. In this orientation, the distance between the distal faces 14A, 16A of the optical fibers 14, 16 and the reflective surfaces 90 of the mirrors 50A, 50B and 50C is indicated by arrow 100. In the neutral state, light emitted by the light sources 74, 76 and 78 into a respective one of the optical fiber pairs 14/62, 16/64 and the third internal optical fiber (not shown)/66 results in a conical beam emerging from the optical fiber and a circular area of light shining on the reflective surface 90.

This is illustrated in FIG. 5 where two of the optical fibers, for example, optical fiber 14, 16 are shown shining a conical light beam 102 that impinges on the reflective surface 90 of the mirrors 50A, 50B and 50C (mirror 50C is indicated, but not shown). Each light beam 102 has a circular intensity or power profile in the plane perpendicular to the longitudinal axis of the catheter body 18 with a diameter at the reflective surface 90 of each of the mirrors 50A, 50B and 50C indicated by arrow 104 that encompasses the central area of light reflectivity 92 ($R_1$) and the first ring of light reflectivity 94 ($R_2$). The reflective surface 90 of each mirror 50A, 50B and 50C reflects a reflected percentage 102A of the power of the conical light beam 102 back toward the distal face 14A of the optical fiber 14, 16 and the third internal optical fiber (not shown). The conically divergent reflected percentage 102A of the light beam 102 has a circular intensity or power profile perpendicular to the longitudinal axis of the catheter body 18 with a diameter at the distal faces 14A, 16A of the optical fibers 14, 16 indicated by line 110.

Since the light beams 102 from the optical fibers 14, 16 still encompass the central area of light reflectivity 92 ($R_1$) and the first ring of light reflectivity 94 ($R_2$), different reflected percentages will reflect off each of those surfaces 92, 94 of each mirror 50A, 50B and 50C. Then, a percentage of the reflected percentage 102A off each of the central area of light reflectivity 92 ($R_1$) and the first ring of light reflectivity 94 ($R_2$) of each mirror 50A, 50B and 50C is captured by each of the optical fibers 14, 16 and the third internal optical fiber (not shown), and travels along those internal optical fibers through the optical connector 56 to the external optical fibers 62, 64 and 66 optically connected to the respective light power detectors 80, 82 and 84 and then the controller 86 shown in FIG. 1. The light power detectors 80, 82 and 84 each detect the power of the light captured by the optical fibers 14, 16 and the third internal optical fiber (not shown) following reflection off the central area of light reflectivity 92 ($R_1$) and the first ring of light reflectivity 94 ($R_2$) of each mirror 50A, 50B and 50C and sends that information to the controller 86. The central area of light reflectivity 92 ($R_1$) and the first ring of light reflectivity 94 ($R_2$) reflect different percentages of the power of the light beam 102, which the light power detectors 80, 82 and 84 are programmed to detect. The controller 86 is further programmed to use the captured percentage of the reflected percentage 102A off each of the central area of light reflectivity 92 ($R_1$) and the first ring of light reflectivity 94 ($R_2$) of each mirror 50A, 50B and 50C as an input to calculate the position of the reflective surface 90 and output to the display 88 that no axial or lateral forces are imparted to the ablation head 24.

Similar principals apply regarding the reflectances of the light reflectivities $R_1$, $R_2$, $R_3$ and $R_n$ of the respective central area 92, the first annular ring 94, the second annular ring 96 and the nth annular ring 98 for the mirrors 50A, 50B and 50C shown in FIGS. 3 and 3A, and with respect to the light reflectivities $R_1A$, $R_1B$, $R_1C$ and $R_1D$ of the respective quadrants 92A, 92B, 92C and 92D of the central area of light reflectivity 92, the light reflectivities $R_2A$, $R_2B$, $R_2C$ and $R_2D$ of the respective quadrants 94A, 94B, 94C and 94D of the first ring of light reflectivity 94, the light reflectivities $R_3A$, $R_3B$, $R_3C$ and $R_3D$ of the respective quadrants 96A, 96B, 96C and 96D of the second ring of light reflectivity 96, and the light reflectivities $R_nA$, $R_nB$, $R_nC$ and $R_nD$ of the respective quadrants 98A, 98B, 98C and 98D of the nth ring of light reflectivity of the mirrors 50A', 50'B and 50C' shown in FIGS. 4 and 4A.

Figure 6:
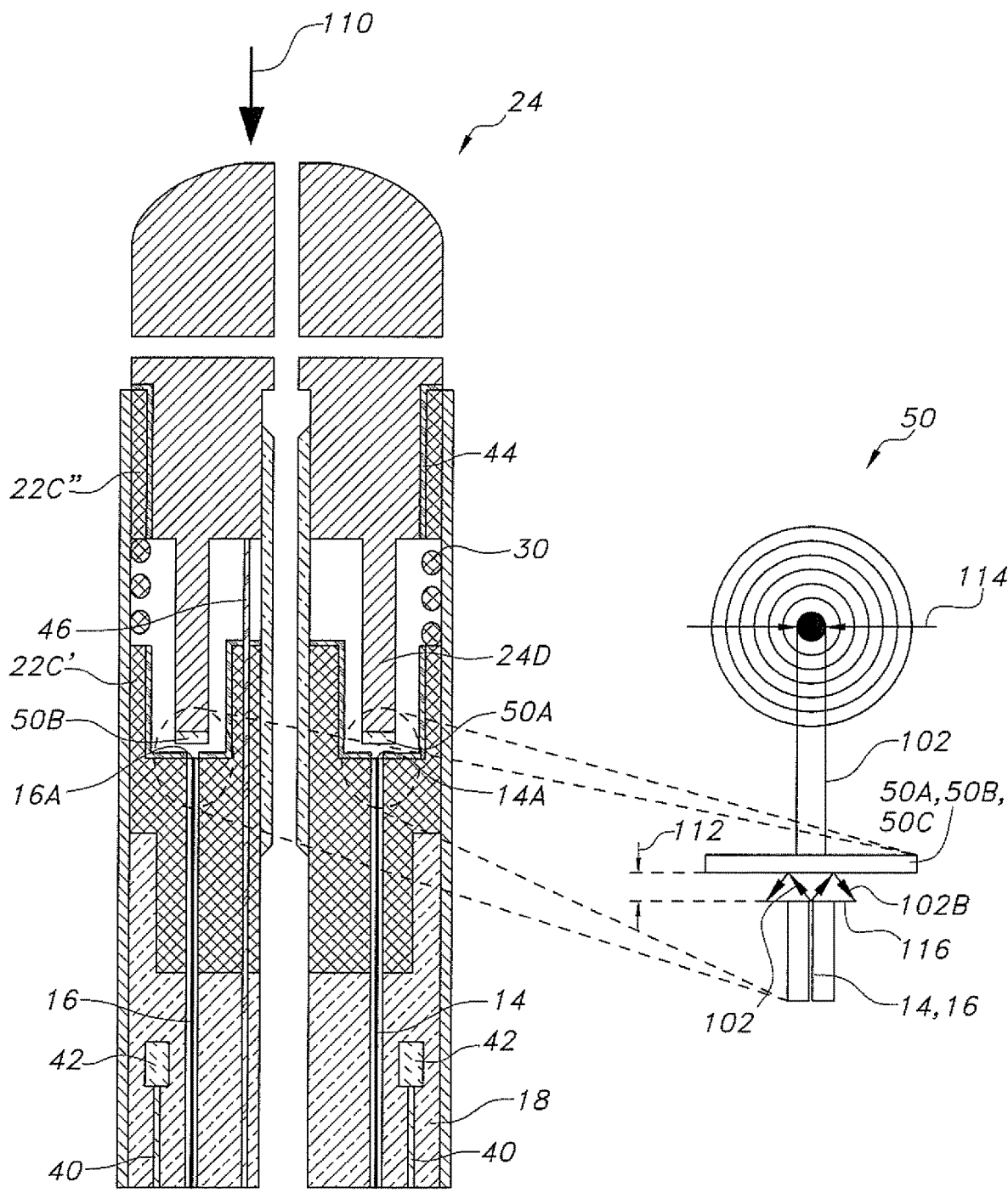
FIG. 6 is a cross-sectional view showing the relative position of two of the mirrors 50A, 50B with respect to the distal faces 14A, 16A of optical fiber 14, 16 with only an axial force but no lateral force imparted to the ablation head 24.

FIG. 6 illustrates the ablation catheter 12 in a second state with only an axial force 110 but no lateral force imparted to the ablation head 24. In this orientation, the distance between the distal faces 14A, 16A of the optical fibers 14, 16 and the third internal optical fiber (not shown), and the reflective surfaces 90 of each of the mirrors 50A, 50B and 50C (mirror 50C is indicated, but not shown) is indicated by numerical designation 112, which is less than distance 100 in FIG. 5. In this second state, a reflected percentage 102B of the light shining from the three internal optical fibers 14, 16 and the third optical fiber (not shown) is reflected by the reflective surfaces 90 of the mirrors 50A, 50B and 50C back to the distal faces 14A, 16A of the optical fibers 14, 16 and the third internal optical fiber (not shown).

Referring still to FIG. 6, the axial force vector 110 is shown causing the spring 30 to compress, which in turn causes the reflective surface 90 of each of the mirrors 50A, 50B and 50C to move proximally along the longitudinal axis of the catheter body 18 so that the mirrors 50A, 50B and 50C are closer to the distal faces 14A, 16A of the optical fibers 14, 16 and the third internal optical fiber (not shown) than in the neutral state shown in FIG. 5 with no axial or lateral force imparted to the ablation head 24. This axial movement of the mirrors 50A, 50B and 50C results in a different reflected percentage 102B of the power of the conical light beam 102 shining toward the distal faces 14A, 16A of the optical fibers 14, 16 and the third internal optical fiber (not shown). The intensity profile of the reflected percentage 102B has a diameter indicated by line 116 reflected toward the plane of the distal faces 14A, 16A of the optical fibers 14, 16.

While line 116 has a smaller diameter than line 110 in FIG. 5, the intensity of the reflected percentage 102B at the distal faces 14A, 16A of the optical fibers 14, 16 and the third internal optical fiber (not shown) is greater than the intensity of the reflected percentage 102A at the distal faces of the optical fibers 14, 16 shown in FIG. 5 because the mirrors 50A, 50B and 50C are closer to the distal faces 14A, 16A of the optical fibers 14, 16 and the third optical fiber (not shown). Then, a percentage of the reflected percentage 1022 is captured by the optical fibers 14, 16 and the third internal optical fiber (not shown) and travels along the internal optical fibers, through the connector 56 to the respective external optical fiber 62, 64 and 66 optically connected to the light power detectors 80, 82 and 84 and then to the controller 86 shown in FIG. 1. The controller 86 is programmed to determine the difference in the intensity or power between the reflected percentages 102B and 102A captured by the internal optical fibers with the position of the mirrors 50A, 50B and 50C in FIG. 5 with respect to the position of the mirrors 50A, 50B and 50C in FIG. 6. The controller 86 is programmed to use that difference as an input to calculate the position of the reflective surfaces 90 and output to the display 88 that an axial force and its magnitude, but no lateral force, is imparted to the ablation head 24.

Similar principals apply regarding the reflectances of the light reflectivities $R_3$ and $R_n$ of the respective second annular ring 96 to the nth annular ring 98 of the mirrors 50A, 50B and 50C shown in FIGS. 3 and 3A, and with respect to the light reflectivities $R_1A$, $R_1B$, $R_1C$ and $R_1D$ of the respective quadrants 92A, 92B, 92C and 92D of the central area of light reflectivity 92, the light reflectivities $R_2A$, $R_2B$, $R_2C$ and $R_2D$ of the respective quadrants 94A, 94B, 94C and 94D of the first ring of light reflectivity 94, the light reflectivities $R_3A$, $R_3B$, $R_3C$ and $R_3D$ of the respective quadrants 96A, 96B, 96C and 96D of the second ring of light reflectivity 96, to the light reflectivities $R_nA$, $R_nB$, $R_nC$ and $R_nD$ of the respective quadrants 98A, 982, 98C and 98D of the nth ring of light reflectivity of the mirrors 50A', 50B' and 50C' shown in FIGS. 4 and 4A.

Figure 7:
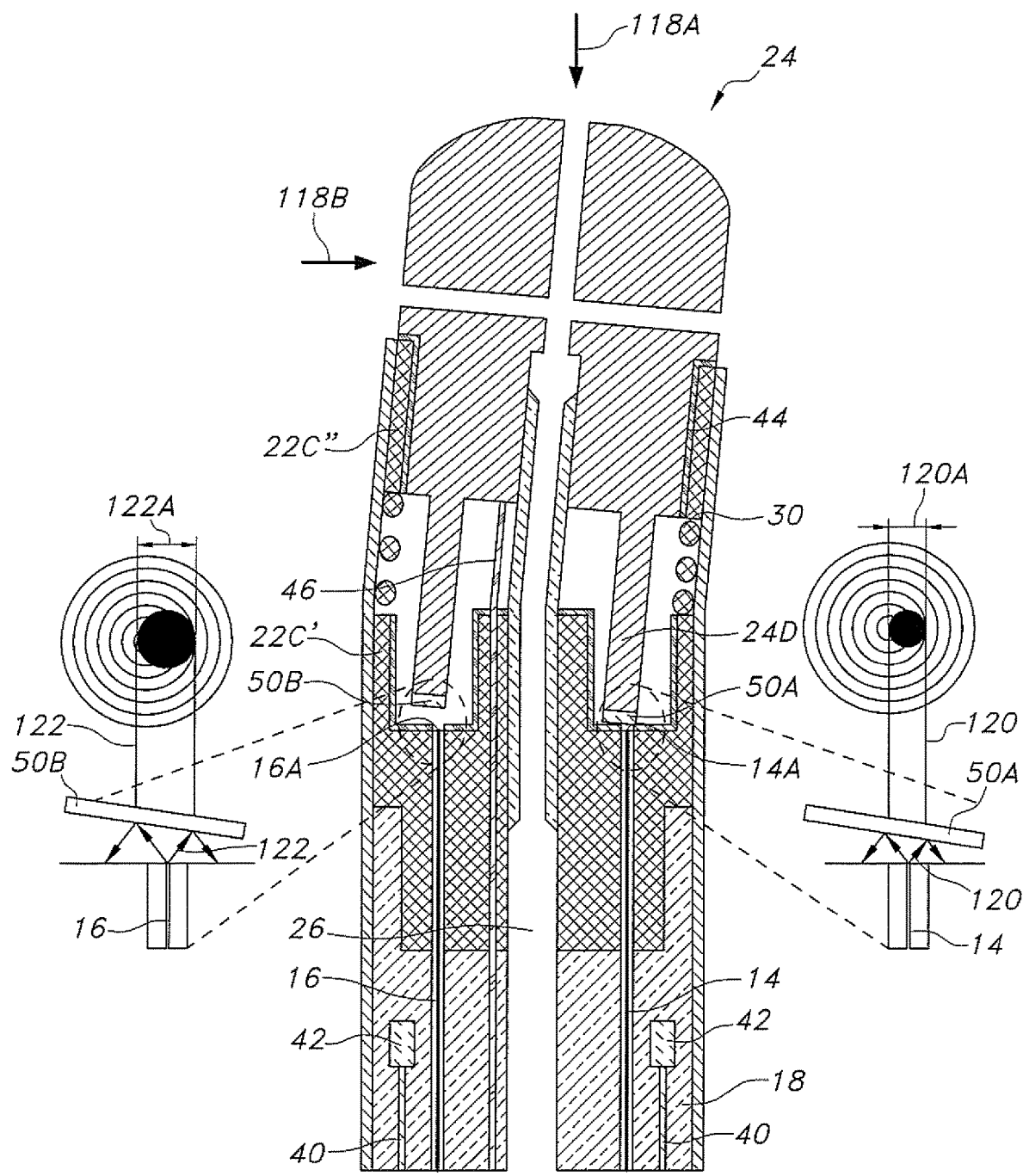
FIG. 7 is a cross-sectional view showing the relative position of two of the mirrors 50A, 50B with respect to the distal faces 14A, 16A of optical fiber 14, 16 with both an axial force 118A and a lateral force 118B imparted to the ablation head 24.
Figure 8:
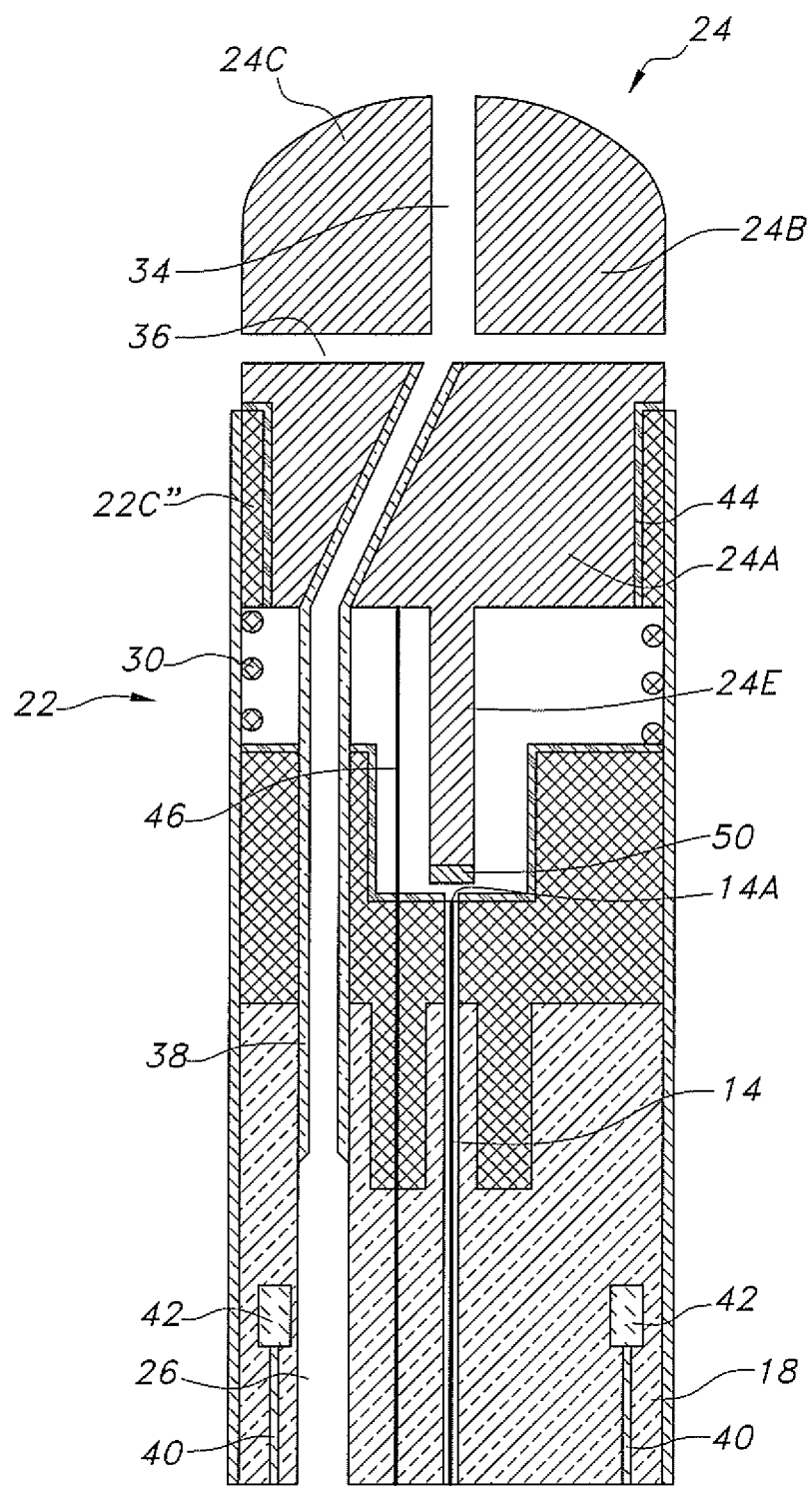
FIG. 8 is a cross-sectional view of another embodiment of an ablation catheter 100 comprising a single optical fiber 14 centered in the catheter and supporting at least three fiber cores (not shown) shining at a mirror 50.
Figure 9:
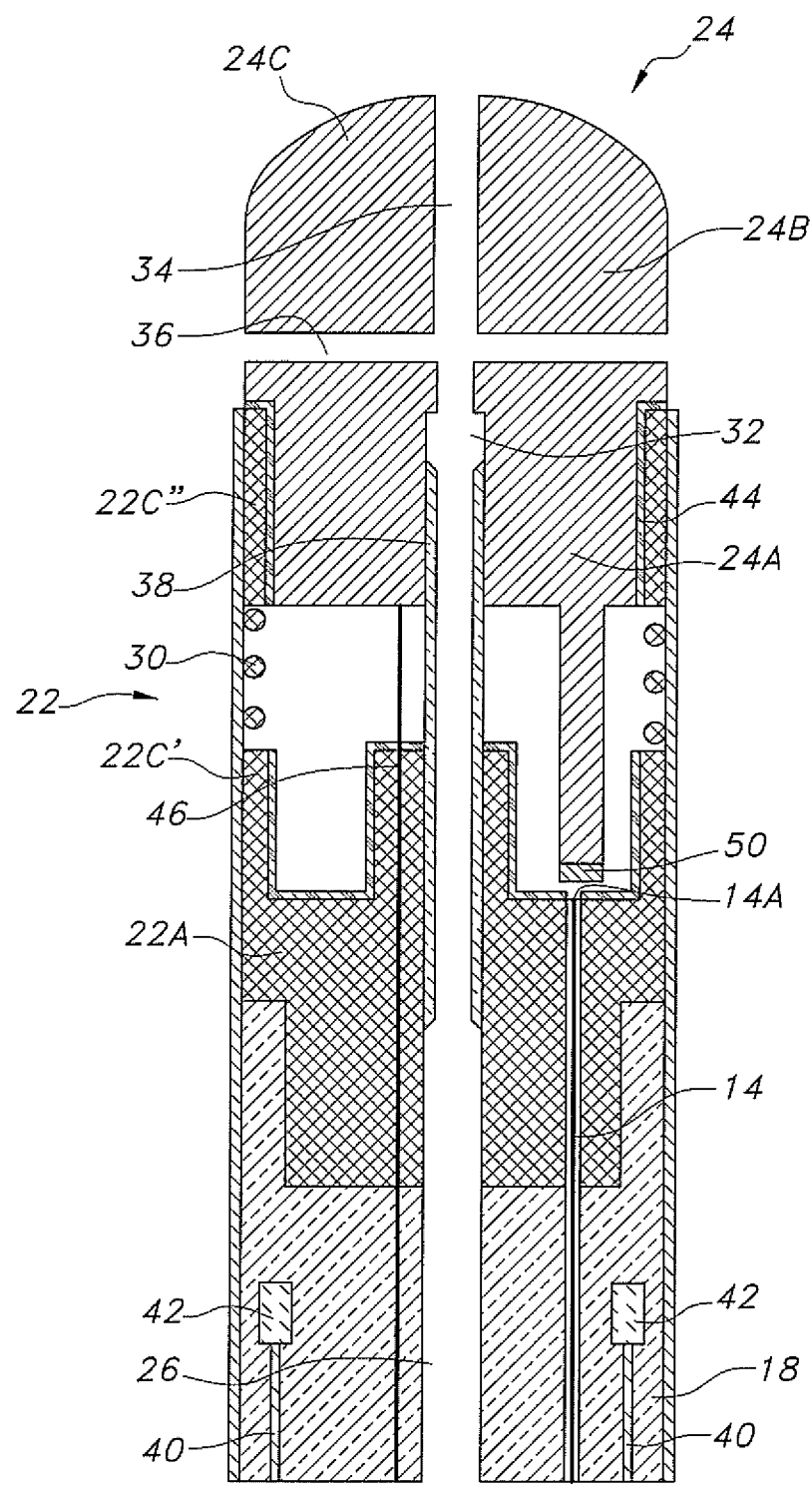
FIG. 9 is a cross-sectional view of another embodiment of an ablation catheter 200 comprising a single optical fiber 14 off-center in the catheter and supporting at least three fiber cores (not shown) shining at a mirror 50.

FIG. 7 illustrates the ablation head 24 being subjected to a force vector having an axial force component 118A and a lateral force component 118B. This causes the ablation head 24 to move laterally and axially with one portion of the spring 30 being compressed more than or less than a diametrically opposed portion of the spring. The light beams 120 and 122 that are emitted by the optical fibers 14, 16 and the third optical fiber (not shown) shine on the reflective surfaces 90 of the mirrors 50A and 50B (mirror 50C is present, but not shown). The respective circular areas of shining light as light areas 120A and 122A. As previously described with respect to FIGS. 5 and 6, with no lateral force component (and either no axial force or only an axial force), light from the optical fibers shins on the central area of light reflectivity 92 and the first ring of light reflectivity 94 of each of the mirrors 50A and 50B. However, this drawing shows that the shining light areas 120A and 122A have shifted on the reflective surfaces 90 of the mirrors 50A and 50B. The light beam 120 from the optical fiber 14 now shins on a portion of the central area of light reflectivity 92 and portions of both the first and second rings of light reflectivity 94 and 96. Simultaneously, the light beam 122 from optical fiber 16 shins on a greater portion of the central area of light reflectivity 92 and greater portions of the first and second rings of light reflectivities 94 and 96. That is because the axial and lateral forces 188A and 118B have caused the ablation head 24 to move laterally toward optical fiber 14 but further away from optical fiber 16. The closer the distance from an optical fiber to the reflective surface of a mirror, the tighter or more confined the shinning light in on the surface of that mirror. Conversely, the further the distance from an optical fiber to the surface of a mirror, the broader or less confined the shinning light is on the reflective surface of the mirror. The light shinning from the third internal optical fiber that is not shown in the drawings is at a different distance from its mirror 50C, which results in a different pattern of light reflectivity from that mirror 50C back to the controller.

Thus, any change in the percentage of light captured by the three internal optical fibers 14, 16 and the third optical fiber (not shown) following reflection from the reflective surfaces 90 of the respective mirrors 50A, 50B and 50C back to the distal faces 14A, 16A of the optical fibers 14, 16 and the third optical fiber (not shown) with respect to the percentages of light captured with the catheter 12 in the first state without an axial force being applied to the ablation head 24 or with respect to the reflected percentages of light captured with the catheter 12 in the second state with only an axial force but no lateral force being imparted to the ablation head 24 is indicative of forces of different axial and lateral magnitudes being applied to the ablation head. Then, relative change of the percentages of light captured by each of the internal optical fibers 14, 16 and the third optical fiber (not shown) is converted by the controller 86 into a value related to the force that the ablation head 24 is exerting against body tissue. The controller 86 is also programmed to calculate a spatial orientation in an x, y, z coordinate system of the ablation head 24 in the vasculature from the relative change of the percentage of light captured by each of the internal optical fibers 14, 16 and the third optical fiber (not shown).

Moreover, change in the percentage of light captured by the three internal optical fibers 14, 16 and the third optical fiber (not shown) following reflection from the reflective surfaces 90 of their respective mirrors 50A, 50B and 50C back to the distal faces 14A, 16A of the optical fibers 14, 16 is with respect to the reflective surfaces shown in FIGS. 3, 3A, 4 and 4A as described above for the state with no axial force imparted to the ablation head 24 shown in FIG. 5 and with respect to the state with only an axial force but no lateral force imparted to the ablation head shown in FIG. 6.

Further, the present invention can be practiced with an ablation catheter having a plurality of optical fibers, for example, more than three optical fibers. Moreover, the three or more optical fibers need not be evenly spaced about the circumference of the annular inner sleeve 24D extending proximally from the cylindrically-shaped proximal head portion 24A of the ablation head 24. So long as the controller 86 is programmed with information related to the relative positions of the plurality of optical fibers and their corresponding mirror, the optical principals described above apply.

In various embodiments of the present ablation catheter 12, the optical fibers 14, 16 are a step index optical fiber, a graded index optical fiber or a photonic crystal optical fiber. In other embodiments of the ablation catheter 12, the optical fibers 14, 16 are a single-mode optical fiber, a multi-mode optical fiber, or a dual clad optical fiber. Still, in other embodiments of the ablation catheter 12, a lens is placed between the distal face 14A, 16A of the optical fiber 14, 16 and the mirrors 50A, 50B to focus the light beam on the reflective surface 90 of the mirror.

In one embodiment of the present ablation catheter 12, the proximal end of the optical fibers 14, 16 and the third internal optical fiber (not shown) are uniformly illuminated by the light sources 74, 76 and 78 to equally excite all bound modes so that the near-field pattern of the emerging light at the distal face 14A, 16A of each of the optical fibers 14, 16 approximates the refractive index profile of the optical fiber. In another embodiment, the light shining from each of the optical fibers 14, 16 and the third internal optical fiber (not shown) passes through a mode scrambler to achieve a uniformly distributed light beam.

Referring back to FIG. 1, this drawing illustrates that there is a visual display 88 connected to the controller 86. As described above, the controller 86 is programmed to calculate the spatial orientation of the ablation head 24 in the vasculature and the force that the ablation head is exerting against body tissue, for example, against myocardial tissue. Among other useful information, the display 88 presents this orientation and force information in real-time in any one of a variety of formats that are useful to the surgeon.

As previously described, during movement of the ablation catheter 12 through the vasculature (both forward and rearward movement), frictional feedback from the surface of the shaft of the catheter dominates the tactile feel in the surgeon's hand while tactile perception of the force acting at the ablation head 24 is minimal. Therefore, there is a risk of vessel injury including perforation due to the force of the catheter 12 including its ablation head 24 against vasculature tissue.

To overcome this, axial and lateral forces applied to the ablation head 24 are not only fed back to the controller 86 for presentation by the display 88 as described above, but the controller also sends a haptic or tactile feedback signal to an electromechanical actuator (not shown) integrated into the handle 20. Haptic or tactile feedback is the use of vibration patterns to convey information to a user or operator. Haptic feedback uses the controller 86 to send haptic feedback signals to the electromechanical actuator, which can be felt by the surgeon holding the handle 20. Exemplary electromechanical actuators include a vibration motor, an eccentric rotating mass (ERM) actuator driven by an electronic circuit, a linear resonant actuator, and a piezoelectric actuator.

In the ablation catheter system 10 of the present invention, an exemplary embodiment has the vibration increase in frequency or amplitude depending on the calculated force of the ablation head 24 against vasculature tissue. Further, the vibrational frequency can be varied to indicate the direction of the force while the amplitude of the vibration can be varied to indicate the magnitude of the axial and lateral force vectors. That way, the surgeon feels the magnitude and direction of the axial and lateral force vectors in his hand as the ablation head 24 of the catheter 12 is moved through the vasculature during a medical procedure.

This haptic or tactile feedback to the surgeon helps reduce the risk of damaging tissue, speeds up the medical procedure and reduces contrast and x-ray use. Also, the haptic or tactile feedback correlates with the contact force of the ablation head against myocardial tissue as ablative energy is imparted to cardiac tissue to create a lesion in the cardiac tissue. The force data at the individual ablations also conveys information on the degree to which the cardiac tissue has been ablated. As discussed above, inaccurate positioning of the ablation head in the myocardia may result in suboptimum ablation or inadvertent ablation of healthy tissue. Excess force between the ablation catheter head and the targeted myocardial tissue may result in excessive ablation, which may permanently damage cardiac muscle and surrounding nerves. Conversely, when the contact force between the ablation head and the targeted myocardial tissue is below a target force, the efficacy of the ablation therapy may be reduced.

It is appreciated that various modifications to the inventive concepts described herein may be apparent to those of ordinary skill in the art without departing from the spirit and scope of the present invention as defined by the appended claims.

What is claimed is:

1. A catheter assembly, comprising:
   a) a catheter, comprising:
      i) a catheter extending along a longitudinal axis from a catheter proximal end to a catheter distal end, wherein a catheter lumen extends to the catheter proximal and distal ends;
      ii) a spring assembly connected to the catheter proximal end, the spring assembly providing a spring assembly lumen extending from a spring assembly proximal end to a spring assembly distal end;
      iii) an electrically energizable ablation head connected to the spring assembly distal end;
      iv) at least a first optical fiber, a second optical fiber and a third optical fiber extending through the catheter and the spring assembly; and
      v) at least a first mirror, a second mirror and a third mirror supported by the ablation head, wherein the first, second and third mirrors face proximally but are spaced distally from a distal face of a corresponding one of the first, second and third optical fibers;
   b) a light source optically configured to emit light of a respective defined power into each of the first, second and third optical fibers;
   c) at least a first light power detector, a second light power detector and a third light power detector optically connected to a corresponding one of the first, second and third optical fibers; and
   d) a controller operatively coupled to the first, second and third light power detectors,
   e) wherein, with the light source emitting light of a respective defined power into each of the at least first, second and third optical fibers shining at a corresponding one of the first, second and third mirrors, and
   f) wherein, in comparison to the catheter with no axial or lateral forces imparted to the ablation head so that the ablation head is aligned with the longitudinal axis of the catheter and the first, second and third mirrors are each spaced a first distance from a distal face of a corresponding one of the first, second and third optical fibers and so that a reflected percentage of light of each of the respective defined powers is reflected by a corresponding one of the first, second and third mirrors back to the distal face of the first, second and third optical fibers with a first percentage of the reflected percentage of the respective defined light power captured by and traveling along each of the first, second and third optical fibers to the corresponding first, second and third light power detector, the first percentage of the reflected percentage being determinable by the controller, with only an axial force imparted to the ablation head to cause the ablation head of the catheter to assume an orientation still aligned with the longitudinal axis of the catheter but with the spring assembly compressed so that each of the first, second and third mirrors is spaced a second distance from the distal face of its corresponding first, second and third optical fiber, the second distance being less than the first distance, a second percentage of the reflected percentage of the respective defined light power is captured by and travels along each of the first, second and third optical fibers to the corresponding first, second and third light power detector, the difference between the first and second percentages of the reflected percentage of the respective defined light power being determinable by the controller to calculate the magnitude of the axial force imparted to the ablation head, and g) wherein, with both axial and lateral forces imparted to the ablation head to cause the ablation head of the catheter and the spring assembly to deflect out of axial alignment with the catheter and with respect to the distal faces of each of the first, second and third optical fibers, the first, second and third mirrors are respectively spaced a third distance from the first optical fiber, a fourth distance from the second optical fiber and a fifth distance from the third optical fiber, the third, fourth and fifth distances being different than the first and second distances and being different than each other, so that in comparison to at least one of the first and second percentages of the reflected percentage of each of the three respective defined light powers, an axial and lateral force induced third percentage of the reflected percentage of the respective defined first, second and third light powers is captured by and travels along the corresponding first, second and third optical fibers to the respective first, second and third light power detectors, and wherein the controller is programmed to use the difference between the first and third percentages or the second and third percentages, or both, of the reflected percentage of the respective defined first, second and third light powers to calculate a magnitude and vector of the axial and lateral forces imparted to the ablation head.

2. The catheter assembly of claim 1, wherein each of the first, second and third mirrors is provided with a patterned reflectance that varies along a radius from a central area of reflectance.

3. The catheter assembly of claim 2, wherein the patterned reflectance of the first, second and third mirrors comprises the central area of reflectance having a first light reflectance $R_1$ and at least one annular ring of reflectance having a second light reflectance $R_2$, and wherein $R_1$ is different than $R_2$, and wherein the first percentages captured by and traveling along each of the first, second and third optical fibers of the reflected percentage of the respective defined first, second and third light powers reflected from the first and second light reflectances $R_1$ and $R_2$ of the respective first, second and third mirrors with no axial or lateral forces imparted to the ablation head in comparison to the second percentages captured by and traveling along each of the first, second and third optical fibers of the reflected percentage of the respective defined first, second and third light powers reflected from the first and second light reflectances $R_1$ and $R_2$ with only an axial force imparted to the ablation head is determinable by the controller to calculate the magnitude of the axial force imparted to the ablation head, and wherein the third percentages captured by and traveling along each of the first, second and third optical fibers of the reflected percentage of the respective defined first, second and third light powers reflected from the first and second light reflectances $R_1$ and $R_2$ of the first, second and third mirrors with both axial and lateral forces imparted to the ablation head in comparison to the first percentages captured by and traveling along the respective first, second and third optical fibers of the reflected percentage of the respective defined first, second and third light powers reflected from the first and second light reflectances $R_1$ and $R_2$ with no axial or lateral forces imparted to the ablation head or, in comparison to the second percentages captured by and traveling along the respective first, second and third optical fibers of the reflected percentage of the respective defined first, second and third light powers reflected from the first and second light reflectances $R_1$ and $R_2$ with only an axial force imparted to the ablation head is determinable by the controller to calculate the magnitude and vector of the axial and lateral forces imparted to the ablation head.

4. The catheter assembly of claim 3, wherein the patterned reflectance of each of the first, second and third mirrors comprises the central area of reflectance having the first light reflectance $R_1$ and at least a first, a second and a third annular rings of reflectance having respective second, third and fourth light reflectances $R_2$, $R_3$ and $R_4$ at progressively greater first, second and third radial distances from the central area of reflectance, and wherein the light reflectances $R_1$, $R_2$, $R_3$ and $R_4$ are different from each other.

5. The catheter assembly of claim 4, wherein the first light reflectance $R_1$ of the central area of reflectance and the second, third and fourth light reflectances $R_2$, $R_3$ and $R_4$ of the respective first, second and third annular rings of reflectance are each divided into quadrants of reflectance, and wherein the quadrants of reflectance of each of the light reflectances $R_1$, $R_2$, $R_3$ and $R_4$ are different from each other.

6. The catheter assembly of claim 4, wherein the first light reflectance $R_1$ of the central area of reflectance of each of the first, second and third mirrors and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

7. The catheter assembly of claim 1, wherein a handle is connected to the catheter proximal end, and wherein at least two push-pull wires extend from the handle to the catheter distal portion.

8. The catheter assembly of claim 7, wherein the handle has an electromechanical actuator, and wherein the controller is programmed to send a haptic vibration signal to the electromechanical actuator.

9. The catheter assembly of claim 8, wherein the electromechanical actuator is selected from the group of a vibration motor, an eccentric rotating mass (ERM) actuator driven by an electronic circuit, a linear resonant actuator, and a piezoelectric actuator.

10. The catheter assembly of claim 8, wherein the controller is programmed to vary at least one of a frequency and an amplitude of the haptic vibration signal to indicate the magnitude and vector of the axial and lateral forces imparted to the atraumatic head.

11. The catheter assembly of claim 7, wherein an optical connector connected to the handle optically connects the controller and first, second and third external optical fibers to the first, second and third optical fiber of the catheter.

12. A catheter assembly, comprising:
   a) a catheter, comprising:
      i) a catheter sidewall extending along a longitudinal axis from a catheter proximal end to a catheter distal end, wherein a catheter lumen extends to the catheter proximal and distal ends;
      ii) a spring assembly connected to the catheter proximal end, the spring assembly providing a spring assembly lumen extending from a spring assembly proximal end to a spring assembly distal end;
      iii) an electrically energizable ablation head connected to the spring assembly distal end;
      iv) at least a first optical fiber, a second optical fiber, and a third optical fiber extending through the catheter and the spring assembly; and
      v) at least a first mirror, a second mirror and a third mirror supported by the ablation head, wherein the first, second and third mirrors face proximally but are spaced distally from a distal face of a corresponding one of the first, second and third optical fibers;
   b) a first light source configured to shine a first defined light power into the first optical fiber, a second light source configured to shine a second defined light power into the second optical fiber, and a third light source configured to shine a third defined light power into the third optical fiber;
   c) a first light power detector optically connected to the first optical fiber, a second light power detector optically connected to the second optical fiber, and a third light power detector optically connected to the third optical fiber; and
   d) a controller operatively coupled to the first, second and third light power detectors,
   e) wherein, with the first, second and third light sources emitting the respective first, second and third light powers into the respective first, second and third optical fibers shining at the respective first, second and third mirrors, and
   f) wherein, in comparison to the catheter with no axial or lateral forces imparted to the ablation head so that the ablation head is aligned with a longitudinal axis of the catheter and the first mirror is spaced a first distance from a distal face of the first optical fiber, the second mirror is spaced a second distance from a distal face of the second optical fiber and the third mirror is spaced a third distance from a distal face of the third optical fiber so that reflected percentages of the first, second and third defined light powers are reflected by the first, second and third mirrors back to the distal face of the respective first, second and third optical fibers with a first percentage of the reflected percentage of the first defined light power captured by and traveling along the first optical fiber to the first light power detector, a second percentage of the reflected percentage of the second defined light power captured by and traveling along the second optical fiber to the second light power detector, and a third percentage of the reflected percentage of the third defined light power captured by and traveling along the third optical fiber to the third light power detector, the first, second and third percentages of the reflected percentages of the first, second and third defined light power being determinable by the controller, with only an axial force imparted to the ablation head of the catheter to cause the ablation head to assume an orientation still axially aligned with the catheter sidewall but with the spring assembly compressed so that the first, second and third mirrors are each spaced a second distance from the distal face of the respective first, second and third optical fiber, the second distance being less than the first distance, a fourth percentage of the reflected percentage of the first defined light power is captured by and travels along the first optical fiber to the first light power detector, a fifth percentage of the reflected percentage of the second defined light power is captured by and travels along the second optical fiber to the second light power detector, and a sixth percentage of the reflected percentage of the third defined light power is captured by and travels along the third optical fiber to the third light power detector, the respective differences between the first and fourth percentages of the reflected percentages of the first defined light power, the second and fifth percentages of the reflected percentages of the second defined light power, and the third and sixth percentages of the reflected percentages of the third defined light power being determinable by the controller to calculate the magnitude of the axial force imparted to the ablation head, and
   g) wherein, with both axial and lateral forces imparted to the ablation head of the catheter to cause the ablation head and the spring assembly to deflect out of axial alignment with the catheter and with respect to the distal face of each of the first, second and third optical fibers, the first, second and third mirrors are spaced a third distance from the first optical fiber, a fourth distance from the second optical fiber and a fifth distance from the third optical fiber, the third, fourth and fifth distances being different than the first and second distances, so that in comparison to the first, second and third percentages of the reflected percentages of the first, second and third defined light powers, an axial and lateral force induced seventh percentage of the reflected percentage of the first defined light power is captured by and travels along the first optical fiber to the first light power detector, an axial and lateral force induced eighth percentage of the reflected percentage of the second defined light power is captured by and travels along the second optical fiber to the second light power detector, and an axial and lateral force induced ninth percentage of the reflected percentage of the third defined light power is captured by and travels along the third optical fiber to the third light power detector, and wherein at least the difference between the first and seventh percentages of the reflected percentage of the first defined light power is different than the differences between the second and eighth percentages of the reflected percentage of the second defined light power and the third and ninth percentages of the reflected percentage of the third defined light power, and wherein the controller is programmed to use the differences between the first and seventh percentages of the reflected first defined light power, the second and eighth percentages of the reflected second defined light power, and the third and ninth percentages of the reflected third defined light power to calculate a magnitude and vector of the axial and lateral forces imparted to the ablation head.

13. The catheter assembly of claim 12, wherein each of the first, second and third mirrors is provided with a patterned reflectance that varies along a radius from a central area of reflectance.

14. The catheter assembly of claim 13, wherein the patterned reflectance of each of the first, second and third mirrors comprises the central area of reflectance having a first light reflectance $R_1$ and at least one annular ring of reflectance having a second light reflectance $R_2$, and wherein $R_1$ is different than $R_2$, and wherein the first percentages of the first defined light power captured by and traveling along the first optical fiber to the first light power detector, the second percentages of the second defined light power captured by and traveling along the second optical fiber to the second light power detector and the third percentages of the third defined light power captured by and traveling along the third optical fiber to the third light power detector from the first and second light reflectances $R_1$ and $R_2$ of the respective first, second and third mirrors with no axial or lateral forces imparted to the ablation head in comparison to the fourth percentages of the first defined light power captured by and traveling along the first optical fiber to the first light power detector, the fifth percentages of the second defined light power captured by and traveling along the second optical fiber to the second light power detector, and the sixth percentages of the third defined light power captured by and traveling along the third optical fiber to the third light power detector from the first and second light reflectances $R_1$ and $R_2$ of the respective first, second and third mirrors with only an axial force imparted to the ablation head is determinable by the controller to calculate the magnitude of the axial force imparted to the ablation head, and wherein the seventh percentages of the first defined light power captured by and traveling along the first optical fiber to the first light power detector, the eighth percentages of the second defined light power captured by and traveling along the second optical fiber to the second light power detector, and the ninth percentages of the third defined light power captured by and traveling along the third optical fiber to the third light power detector from the first and second light reflectances $R_1$ and $R_2$ of the respective first, second and third mirrors with both axial and lateral forces imparted to the ablation head in comparison to the respective first, second and third percentages of the reflected percentages of the first, second and third defined light powers from the first and second light reflectances $R_1$ and $R_2$ of the respective first, second and third mirrors with no axial or lateral forces imparted to the ablation head or, in comparison to the respective fourth, fifth and sixth percentages of the reflected percentages of the first, second and third defined light powers from the first and second light reflectances $R_1$ and $R_2$ of the first, second and third mirrors with only an axial force imparted to the ablation head is determinable by the controller to calculate the magnitude and vector of the axial and lateral forces imparted to the ablation head.

15. The catheter assembly of claim 12, wherein the patterned reflectance of each of the first, second and third mirrors comprises the central area of reflectance having the first light reflectance $R_1$ and at least a first, a second and a third annular rings of reflectance having respective second, third and fourth light reflectances $R_2$, $R_3$ and $R_4$ at progressively greater first, second and third radial distances from the central area of reflectance, and wherein the light reflectances $R_1$, $R_2$, $R_3$ and $R_4$ are different from each other.

16. The catheter assembly of claim 15, wherein the first light reflectance $R_1$ of the central area of reflectance of each of the first, second and third mirrors and the second, third and fourth light reflectances $R_2$, $R_3$ and $R_4$ of the respective first, second and third annular rings of reflectance are each divided into quadrants of reflectance, and wherein the quadrants of reflectance of each of the light reflectances $R_1$, $R_2$, $R_3$ and $R_4$ are different from each other.

17. The catheter assembly of claim 15, wherein the first light reflectance $R_1$ of the central area of reflectance of each of the first, second and third mirrors and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

18. The catheter assembly of claim 12, wherein the first, second and third optical fibers are evenly spaced at 120° intervals about the catheter.

19. The catheter assembly of claim 12, wherein the first, second and third light sources are individually selected from a Superluminescent Light Emitting Diode (SLED), a scanning laser and a narrow linewidth laser.

20. The catheter assembly of claim 12, wherein the spring assembly comprises a coil spring or a slotted spring.

21. The catheter assembly of claim 12, wherein the controller is further programmed to calculate an orientational value of the ablation head with respect to its axial alignment or non-alignment with the catheter from any one of:
  a) the first percentage of the reflected percentage of the first defined light power captured by and traveling along the first optical fiber to the first light power detector, the second percentage of the reflected percentage of the second defined light power captured by and traveling along the second optical fiber to the second light power detector, and the third percentage of the reflected percentage of the third defined light power captured by and traveling along the third optical fiber to the third light power detector with no axial force imparted to the ablation head;
  b) the fourth percentage of the reflected percentage of the first defined light power captured by and traveling along the first optical fiber to the first light power detector, the fifth percentage of the reflected percentage of the second defined light power captured by and traveling along the second optical fiber to the second light power detector, and the sixth percentage of the reflected percentage of the third defined light power captured by and traveling along the third optical fiber to the third light power detector with only the axial force imparted to the ablation head; and
  c) the seventh percentage of the reflected percentage of the first defined light power captured by and traveling along the first optical fiber to the first light power detector, the eighth percentage of the reflected percentage of the second defined light power captured by and traveling along the second optical fiber to the second light power detector, and the ninth percentage of the reflected percentage of the third defined light power captured by and traveling along the third optical fiber to the third light power detector with both axial and lateral forces imparted to the ablation head.

22. A catheter, comprising:
  a) a catheter body extending along a longitudinal axis from a catheter body proximal end to a catheter body distal end, wherein a catheter lumen extends to the catheter body proximal and distal ends;

b) a spring assembly connected to the catheter body proximal end, the spring assembly providing a spring assembly lumen extending from a spring assembly proximal end to a spring assembly distal end;
c) an electrically energizable ablation head connected to the spring assembly distal end;
d) at least a first optical fiber, a second optical fiber and a third optical fiber extending through the catheter and the spring assembly; and
e) at least a first mirror, a second mirror and a third mirror supported by the ablation head, wherein the first, second and third mirrors face proximally but are spaced distally from a distal face of a corresponding one of the first, second and third optical fibers, and wherein each of the first, second and third mirrors is provided with a patterned reflectance that varies along a radius from a central area of reflectance.

23. The catheter of claim 22, wherein the patterned reflectance of each of the first, second and third mirrors comprises the central area of reflectance having a first light reflectance $R_1$ and at least one annular ring of reflectance having a second light reflectance $R_2$, and wherein $R_1$ is different than $R_2$.

24. The catheter of claim 23, wherein the first light reflectance $R_1$ of the central area of reflectance of each of the first, second and third mirrors and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

25. A catheter, comprising:
a) a catheter body extending along a longitudinal axis from a catheter body proximal end to a catheter body distal end, wherein a catheter lumen extends to the catheter body proximal and distal ends;
b) a spring assembly connected to the catheter body proximal end, the spring assembly providing a spring assembly lumen extending from a spring assembly proximal end to a spring assembly distal end;
c) an electrically energizable ablation head connected to the spring assembly distal end;
d) at least one optical fiber extending through the catheter and the spring assembly, wherein at least three fiber cores extend through the optical fiber to a distal face of the optical fiber; and
e) at least one mirror supported by the ablation head, wherein the mirror faces proximally but is spaced distally from the at least three fiber cores at the distal face of the optical fiber, and wherein the mirror is provided with a patterned reflectance that varies along a radius from a central area of reflectance.

26. The catheter of claim 25, wherein the patterned reflectance of the mirror comprises the central area of reflectance having a first light reflectance $R_1$ and at least one annular ring of reflectance having a second light reflectance $R_2$, and wherein $R_1$ is different than $R_2$.

27. The catheter of claim 26, wherein the first light reflectance $R_1$ of the central area of reflectance of the mirror and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

28. The catheter of claim 25, wherein the at least one optical fiber supporting the at least three fiber cores is either aligned along a longitudinal axis of the catheter or it is off-center with respect to the longitudinal axis.

* * * * *